US010330610B2

(12) United States Patent
Charvat et al.

(10) Patent No.: US 10,330,610 B2
(45) Date of Patent: Jun. 25, 2019

(54) METHODS AND APPARATUS FOR IMAGING OF NEAR-FIELD OBJECTS WITH MICROWAVE OR TERAHERTZ RADIATION

(71) Applicants:Massachusetts Institute of Technology, Cambridge, MA (US); Board of Trustees of Michigan State University, East Lansing, MI (US)

(72) Inventors: Gregory Charvat, Guilford, CT (US); Andrew Temme, Saint Paul, MN (US); Micha Feigin-Almon, Somerville, MA (US); Ramesh Raskar, Cambridge, MA (US); Hisham Bedri, Newton, MA (US)

(73) Assignees: Massachusetts Institute of Technology, Cambridge, MA (US); Board of Trustees of Michigan State University, East Lansing, MI (US)

( * ) Notice: Subject to any disclaimer, the term of this patent is extended or adjusted under 35 U.S.C. 154(b) by 316 days.

(21) Appl. No.: 15/266,195

(22) Filed: Sep. 15, 2016

(65) Prior Publication Data
US 2017/0212059 A1    Jul. 27, 2017

Related U.S. Application Data

(60) Provisional application No. 62/219,625, filed on Sep. 16, 2015.

(51) Int. Cl.
*G01N 22/00* (2006.01)
*G01S 13/88* (2006.01)
*G01N 21/3586* (2014.01)

(52) U.S. Cl.
CPC ......... *G01N 22/00* (2013.01); *G01N 21/3586* (2013.01); *G01S 13/88* (2013.01); *G01S 13/887* (2013.01)

(58) Field of Classification Search
CPC .... G01N 22/00; G01N 21/3586; G01S 13/88; G01S 13/885; G01S 13/887; G01S 13/888
See application file for complete search history.

(56) References Cited

U.S. PATENT DOCUMENTS 3,713,156 A * 1/1973 Pothier ..................... G01S 7/04
                                                                342/179
4,910,523 A * 3/1990 Huguenin ............... G01S 7/024
                                                                250/332

(Continued)

OTHER PUBLICATIONS

Bonetti, J., et al., Transition Edge Sensor Focal Plane Arrays for the BICEP2, Keck, and Spider CMB Polarimeters; published in IEEE Transactions on Applied Superconductivity (vol. 21, Issue 3, Jun. 2011), pp. 219-222.

(Continued)

*Primary Examiner* — Peter M Bythrow
(74) *Attorney, Agent, or Firm* — Stephen R. Otis

(57) ABSTRACT

An imaging system images near-field objects with focused microwave or terahertz radiation. Multiple antennas emit microwave or terahertz radiation, such that the radiation varies in frequency over time, illuminates a near-field object, reflects from the near-field object, and travels to a passive aperture. For example, the passive aperture may comprise a dielectric lens or a parabolic reflector. The passive aperture focuses, onto a spatial region, the microwave or terahertz radiation that reflected from the near-field object. One or more antennas take measurements, in the spatial region, of the microwave or terahertz radiation that reflected from the near-field object. A computer calculates, based on the measurements, an image of the near-field object and depth information regarding the near-field object.

4 Claims, 13 Drawing Sheets

(56) References Cited

U.S. PATENT DOCUMENTS

| | | | | |
|---|---|---|---|---|
| 5,047,783 | A * | 9/1991 | Hugenin | G01S 7/024 250/332 |
| 5,227,800 | A * | 7/1993 | Huguenin | G01S 7/024 250/332 |
| 5,557,283 | A * | 9/1996 | Sheen | G01S 13/887 342/179 |
| 5,829,437 | A | 11/1998 | Bridges | |
| 5,835,054 | A * | 11/1998 | Warhus | G01S 7/292 342/22 |
| 6,057,761 | A * | 5/2000 | Yukl | A61B 5/0507 250/358.1 |
| 6,061,589 | A | 5/2000 | Bridges et al. | |
| 6,130,637 | A | 10/2000 | Meszaros et al. | |
| 6,166,681 | A | 12/2000 | Meszaros et al. | |
| 6,480,141 | B1 | 11/2002 | Toth et al. | |
| 6,507,309 | B2 * | 1/2003 | McMakin | G01S 7/20 342/179 |
| 6,777,684 | B1 * | 8/2004 | Volkov | G01N 21/3581 250/341.1 |
| 6,870,162 | B1 * | 3/2005 | Vaidya | H04N 5/217 250/330 |
| 6,965,340 | B1 * | 11/2005 | Baharav | G01S 13/89 342/175 |
| 7,034,746 | B1 * | 4/2006 | McMakin | G01S 7/024 342/175 |
| 7,119,731 | B2 * | 10/2006 | Fleisher | G01S 13/887 342/22 |
| 7,145,506 | B2 * | 12/2006 | Holt | G01S 13/89 342/179 |
| 7,194,236 | B2 * | 3/2007 | Lovberg | G01S 13/887 250/252.1 |
| 7,212,153 | B2 * | 5/2007 | Rowe | G01S 13/887 342/179 |
| 7,253,766 | B2 * | 8/2007 | Foote | G01S 13/003 342/179 |
| 7,298,318 | B2 * | 11/2007 | Baharav | G01S 13/04 342/179 |
| 7,365,672 | B2 * | 4/2008 | Keller | G01N 21/3581 342/179 |
| 7,405,692 | B2 * | 7/2008 | McMakin | G01S 7/20 342/22 |
| 7,415,244 | B2 * | 8/2008 | Kolinko | G01V 8/005 342/179 |
| 7,804,442 | B2 * | 9/2010 | Ammar | G01S 17/89 342/179 |
| 7,844,081 | B2 * | 11/2010 | McMakin | G01S 13/887 382/115 |
| 8,248,293 | B2 * | 8/2012 | Kroning | G01S 7/025 342/118 |
| 8,253,619 | B2 * | 8/2012 | Holbrook | H04N 1/107 324/323 |
| 9,448,187 | B2 * | 9/2016 | Ostadrahimi | G01N 22/00 |
| 2004/0056790 | A1 * | 3/2004 | Lovberg | G01S 13/887 342/22 |
| 2004/0080448 | A1 * | 4/2004 | Lovberg | G01S 13/887 342/22 |
| 2006/0017605 | A1 * | 1/2006 | Lovberg | G01K 7/226 342/22 |
| 2006/0066469 | A1 * | 3/2006 | Foote | G01S 13/003 342/22 |
| 2007/0102629 | A1 * | 5/2007 | Richard | G01S 7/024 250/225 |
| 2007/0263907 | A1 * | 11/2007 | McMakin | G01S 13/887 382/115 |
| 2009/0058710 | A1 * | 3/2009 | Levitan | G01S 7/024 342/22 |
| 2009/0073023 | A1 * | 3/2009 | Ammar | G01S 13/887 342/22 |
| 2009/0289833 | A1 * | 11/2009 | Johnson | G01S 7/35 342/118 |
| 2010/0214150 | A1 * | 8/2010 | Lovberg | G01K 11/006 342/22 |
| 2011/0043403 | A1 * | 2/2011 | Loffler | G01S 7/02 342/25 A |
| 2011/0234783 | A1 * | 9/2011 | Uemura | G01S 7/412 348/77 |
| 2012/0307967 | A1 * | 12/2012 | Smith | G01V 5/0016 378/57 |
| 2013/0335256 | A1 * | 12/2013 | Smith | G01S 13/887 342/22 |
| 2014/0055314 | A1 * | 2/2014 | Rappaport | H01Q 15/16 343/840 |
| 2014/0368373 | A1 * | 12/2014 | Crain | G01S 5/02 342/5 |
| 2015/0285907 | A1 * | 10/2015 | Mohamadi | H01Q 3/24 342/21 |
| 2015/0369756 | A1 * | 12/2015 | Rezgui | G01N 22/00 702/57 |

OTHER PUBLICATIONS

Chan, W., et al., A single-pixel terahertz imaging system based on compressed sensing; published in Applied Physics Letters, vol. 93, Issue 12 (2008).

De Jonge, C., et al., Development of a passive stand-off imager using MKID technology for security and biomedical applications; published in 2012 37th International Conference onInfrared, Millimeter, and Terahertz Waves (IRMMW-THz).

Erickson, N., et al., A 15 Element Focal Plane Array for 100 GHz; published in IEEE Transactions on Microwave Theory and Techniques (vol. 40, Issue 1, Jan. 1992), pp. 1-11.

Erickson, N., et al., A cryogenic focal plane array for 85-115 GHz using MMIC preamplifiers; published in IEEE Transactions on Microwave Theory and Techniques (vol. 47, Issue 12, Dec. 1999), p. 2212-2219.

Fernandes, C., Shaped dielectric lenses for wireless millimeter-wave communications; published in IEEE Antennas and Propagation Magazine (vol. 41, Issue 5, Oct. 1999), p. 141-150.

Ghasr, M., et al., Portable Real-Time Microwave Camera at 24 GHz; published in IEEE Transactions on Antennas and Propagation (vol. 60, Issue 2, Feb. 2012), pp. 1114-1125.

Goldsmith, P., Focal plane arrays for millimeter-wavelength astronomy; published in IEEE MTT-S International Microwave Symposium Digest, 1992.

Hunt, J., et al., Metamaterial Apertures for Computational Imaging; published in Science (Jan. 2013), vol. 339, Issue 6117, pp. 310-313.

Kapilevich, B., et al., Millimeter Waves Sensing Behind Walls—Feseability Study with FEL Radiation; published in Proceedings of FEL 2007, Novosibirsk, Russia.

Locke, L., et al., Novel K-band prime focus reflector-coupled focal plane array; published in 2013 European Microwave Conference (EuMC).

Rodriguez_Morales, F., et al., A terahertz focal plane array using HEB superconducting mixers and MMIC IF amplifiers; published in IEEE Microwave and Wireless Components Letters (vol. 15, Issue 4, Apr. 2005), pp. 199-201.

Sandri, M., et al., A view on the Planck LFI optics; published in 2010 Proceedings of the Fourth European Conference onAntennas and Propagation (EuCAP).

Shirikoff, E., et al., The South Pole Telescope SZ-Receiver Detectors; published in IEEE Transactions on Applied Superconductivity (vol. 19, Issue 3, Jun. 2009), pp. 517-519.

Spinoulas, L., et al., Optimized compressive sampling for passive millimeter-wave imaging; published in Applied Optics vol. 51, Issue 26, pp. 6335-6342 (2012).

Tang, A., et al., A 200 GHz 16-pixel Focal Plane Array Imager using CMOS Super Regenerative Receivers with Quench Synchronization; published in 2012 IEEE MTT-S InternationalMicrowave Symposium Digest (MTT).

Yassin, G., et al., Easy to fabricate feeds for astronomical receivers; published in 2013 International Workshop onAntenna Technology (iWAT).

* cited by examiner

METHODS AND APPARATUS FOR IMAGING OF NEAR-FIELD OBJECTS WITH MICROWAVE OR TERAHERTZ RADIATION

RELATED APPLICATIONS

This application claims the benefit of U.S. Provisional Patent Application No. 62/219,625, filed Sep. 16, 2015, the entire disclosure of which is herein incorporated by reference.

STATEMENT REGARDING FEDERALLY SPONSORED RESEARCH OR DEVELOPMENT

This invention was made with government support under Grant No. 0802267 awarded by the National Science Foundation Graduate Research Fellowship. The government has certain rights in the invention.

FIELD OF TECHNOLOGY

The present invention relates generally to imaging of near-field objects with focused microwave or terahertz radiation.

COMPUTER PROGRAM LISTING

Attached are four ASCII text files: (1) range_boundaries_vectorized.txt, created Sep. 11, 2016 with a size of about 4 KB; (2) microwave_camera_read_data.txt, created Sep. 11, 2016 with a size of about 3 KB; (3) microwave_camera_read_data_cal2.txt created Sep. 11, 2016 with a size of about 8 KB; and (4) microwave_camera_multispectral_cal4.txt created Sep. 11, 2016 with a size of about 13 KB. These four ASCII text files comprise source code for software employed in a prototype implementation of this invention. These four ASCII text files are each incorporated by reference herein.

BACKGROUND

Definitions

As used herein, "terahertz frequency band" means the frequency band that is greater than 0.3 THz and less than or equal to 390 THz.

As used herein, "microwave frequency band" means the frequency band that is greater than or equal to 300 MHz and less than or equal to 300 GHz.

Problems with Imaging Using Microwave or Terahertz Radiation

Microwave or terahertz radiation can penetrate many obstructions that are opaque at visible light wavelengths. However, imaging with such radiation suffers from two problems: (1) resolution limits associated with relatively small apertures and (2) unrecoverable "stealth" regions. The "stealth" regions occur as a result of the specularity of many objects at microwave or terahertz frequencies.

SUMMARY

In illustrative implementations of this invention, a microwave or terahertz imaging system solves these two problems.

First, the system includes a large passive aperture that improves lateral resolution. The passive aperture focuses the microwave or terahertz radiation unto a focal plane. One or more antennas sample the radiation at the focal plane, in a sampling region that is smaller than the passive aperture.

Second, the system includes multiple microwave or terahertz transmitters that illuminate the scene with radiation from multiple angles. One or more computers process sensor data gathered under this multi-angle illumination, in order to output an image in which stealth regions are reduced.

The passive aperture may comprise a reflective surface, such as a parabolic reflector. Alternatively, the passive aperture may comprise a dielectric lens.

In illustrative implementations, the passive aperture (e.g., reflective surface or dielectric lens) focuses microwave or terahertz radiation from a near-field object unto a focal plane.

An advantage of focusing the radiation onto a focal plane is that the size of the region to be sampled is thereby reduced. Thus, a large aperture may be employed (in order to increase lateral resolution), while sampling only a small region in the focal plane.

Because the passive aperture focuses the radiation onto a spatial region that is smaller than the passive aperture itself, the number of measurements needed to sample the focused radiation in this spatial region is less than would be needed to sample unfocused radiation over the entire aperture. Thus, sampling radiation at a focal plane avoids the larger number of measurements, extra complexity, extra expense and additional computing that would be needed if the entire aperture itself were actively sampled.

Another advantage of focusing the microwave or terahertz radiation onto a focal plane is that the focused radiation may be sampled at the focal plane in a manner that facilitates compressive sensing, coded aperture sensing and other computational imaging techniques.

For example, in some implementations of this invention, a microwave or terahertz imaging system performs compressive sensing based on samples taken at the focal plane. The compressive sensing algorithm may reconstruct an accurate image of a scene, even though the number of samples (measurements) taken at the focal plane is much less than the number of pixels in the computed image.

In some other implementations of this invention, a microwave or terahertz imaging system performs coded aperture sensing based on samples taken at the focal plane. In the coded aperture sensing, a spatial radiation modulator (e.g., a mask) selectively attenuates microwave or terahertz radiation from the object being imaged, causing the radiation to be attenuated in a known spatial pattern before the radiation reaches the antenna or antennas that measure the radiation. For example, the spatial radiation modulator employed in the coded aperture sensing may be positioned at the focal plane and may comprise a FZP (fresnel zone plate) mask, a ORA (optimized random pattern) mask, an URA (uniformly redundant array) mask, a HURA (hexagonal uniformly redundant array) mask, a MURA (modified uniformly redundant array) mask, a Levin mask, or a Veeraraghavan mask.

In illustrative implementations, the imaging system is focused at a near-field depth.

In illustrative implementations, one or more antennas located at the focal plane measure microwave or terahertz radiation that is reflected from the scene. For example, in some cases, an "on-chip" sensor array includes multiple antennas that are located at the focal plane and that sample the radiation incident on the focal plane. In other cases, a reconfigurable sensor, which includes at least one antenna located at the focal plane, samples the radiation incident on the focal plane. In yet other cases, a mechanical raster scan is performed: actuators move an antenna to different points in the focal plane, such that radiation incident at different points in the focal plane is sampled by the antenna at different times.

In illustrative implementations, the imaging system determines the depth of points in the scene. For example, the system may employ FMCW (frequency-modulated continuous-wave) depth detection. Specifically, the transmitters may emit FMCW microwave or terahertz radiation; one or more antennas may gather sensor data regarding the radiation that reflects from the scene; and one or more computers may analyze the data to extract depth information. In some cases, the FMCW radiation comprises chirps. The chirps are frequency sweeps, in which the frequency of the emitted microwave or terahertz radiation increases linearly over time or decreases linearly over time. Alternatively, other waveforms may be employed for depth detection. For example, the transmitters may emit microwave or terahertz radiation that comprises impulse waveforms, noise waveforms, code division multiple access (CDMA) waveforms, pulsed CW (continuous wave) waveforms, Barker Coded waveforms, or any arbitrary time varying waveform. These waveforms may vary over time in frequency, amplitude or phase or any combination thereof.

In illustrative implementations, the radiation that is sampled at the focal plane (e.g., a reflected chirp) is multispectral. Because scattered returns from most target scenes are frequency dependent, providing different quantities of scattered signal at different wavelengths, the multi-spectral images provide more information about the scene than would be obtainable from single frequency images (all other factors being equal).

In some implementations of this invention, a microwave or terahertz imaging system images a near-field object that is behind a partition which is opaque to visible light (such as dry-wall or plywood). The sensors that sample the focal plane may have such a high temporal resolution that they distinguish the different times of arrival for radiation that travels different round-trip distances to and from points at different scene depths. As a result, the sensor data may be "time-gated" by (a) disregarding frames that correspond to the time at which radiation that reflects from the partition arrives at the focal plane, and (b) calculating an image based on other frames. Thus, even a large reflection from the partition may be removed from an image, by disregarding frames that include reflection from the partition and by calculating the image from other frames.

In illustrative implementations, the imaging system samples microwave or terahertz radiation at multiple points in the focal plane, and outputs images of a scene that appear "camera-like". For example, the imaging system may produce images that recover, from microwave or terahertz radiation reflected from a near-field object, the 2D brightness, depth, and multi-spectral response of that object.

Advantageously, in illustrative implementations, this invention may be implemented with low cost hardware.

This invention has many practical applications. For example, in some implementations, this invention may be employed: (a) in autonomous vehicles, for imaging the surroundings of the vehicle and for detecting distance between the vehicle and objects in the vicinity of the vehicle; (b) to image everyday objects in the microwave or terahertz frequency band; (c) to image objects that are behind material that is opaque to visible light, including imaging victims hidden in building rubble after an earthquake, (d) for non-destructive testing; and (e) for imaging in hazardous conditions.

The description of the present invention in the Summary and Abstract sections hereof is just a summary. It is intended only to give a general introduction to some illustrative implementations of this invention. It does not describe all of the details and variations of this invention. Likewise, the Title of this document does not limit the invention in any way; instead the Title is merely a general, non-exclusive way of referring to this invention. This invention may be implemented in many other ways.

BRIEF DESCRIPTION OF THE DRAWINGS

In FIG. 2B, the wavelength is shorter than in FIG. 2A.

FIG. 5A is a front view of the system; FIG. 5B is a side view of the system.

FIG. 6A is a front view of the system; FIG. 6B is a side view of the system.

In FIG. 6C, the front side of the "on-chip" sensor array is visible. In FIG. 6D, the back side of the "on-chip" sensor array is visible.

In FIG. 6E, the reconfigurable sensor array includes switchable antennas. In FIG. 6F, the reconfigurable sensor array includes a programmable mask.

The above Figures show some illustrative implementations of this invention, or provide information that relates to those implementations. However, this invention may be implemented in many other ways.

DETAILED DESCRIPTION

General

In illustrative implementations of this invention, an imaging system images near-field objects with focused microwave or terahertz radiation.

Figure 1:
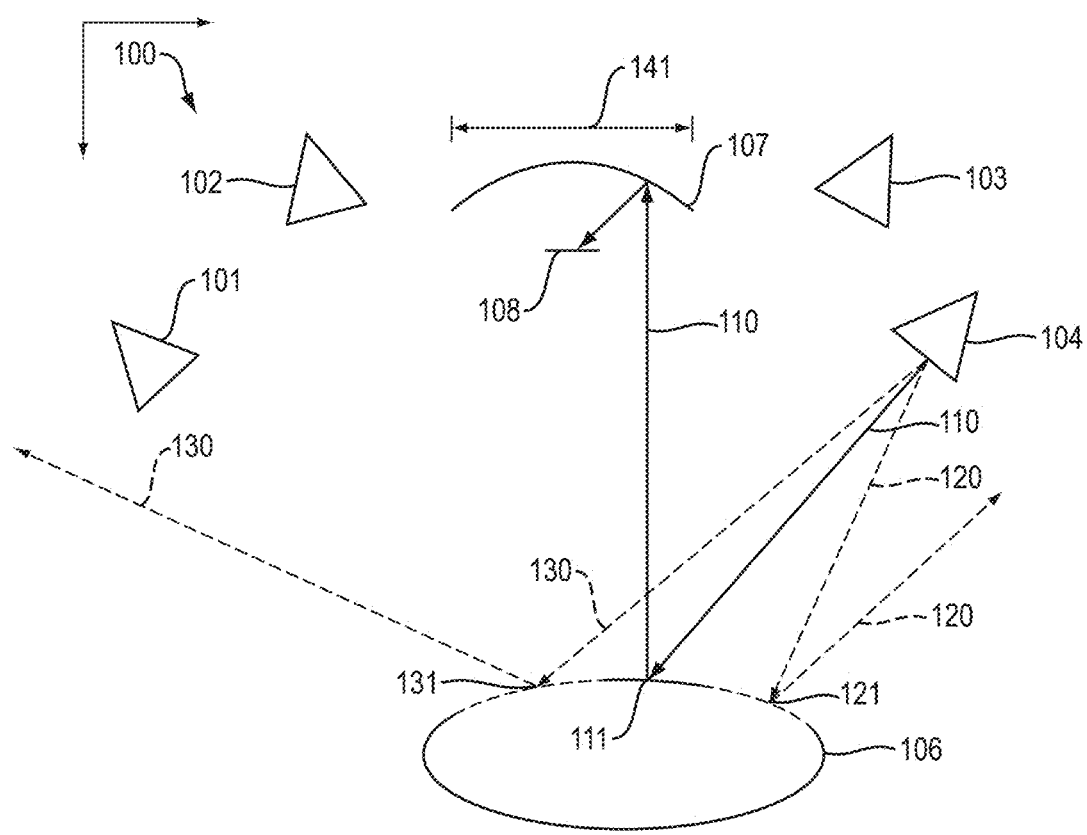
FIG. 1 shows a microwave or terahertz imaging system that includes multiple transmitters and a parabolic reflector that focuses radiation onto a focal plane.

FIG. 1 shows a microwave or terahertz imaging system 100, in an illustrative implementation of this invention. The imaging system 100 includes multiple transmitters 101, 102, 103, 104 and a parabolic reflector 107 that focuses radiation onto a focal plane 108. The transmitters 101, 102, 103, 104 emit microwave or terahertz radiation sequentially, one transmitter at a time.

FIG. 1 shows the imaging system 100 at a time when transmitter 104 is emitting microwave or terahertz radiation, including rays 110, 120 and 130. Rays 120 and 130 (a) reflect off of points 121 and 131 respectively of near-field object 106; and (b) never reaches focal plane 108. However, ray 110 travels to and then reflects from point 111 of object 106, then travels to and reflects from parabolic reflector 107, and then travels to focal plane 108. Ray 110 is not the only ray from transmitter 104 that reaches focal plane 108: multiple rays of microwave or terahertz radiation from transmitter 104 reflect from object 106 and then are focused by the parabolic reflector 107 onto focal plane 108.

There are several advantages of employing multiple transmitters 101, 102, 103, 104. First, even if radiation emitted by a transmitter is blocked by an occluder, radiation from the other transmitters may reach the focal plane. Second, data samples of reflections from multiple transmitters may be computationally fused in such a manner as to reduce "stealth regions", as described in more detail below.

An antenna or array of antennas (not shown in FIG. 1) is located at focal plane 108 and samples the microwave or terahertz radiation that is incident on the focal plane 108 and that has been focused by parabolic reflector 107 unto the focal plane 108.

The maximum dimension 141 of parabolic reflector 107 is equal to the largest diameter of parabolic reflector 107.

In illustrative implementations of this invention, the imaging system samples microwave or terahertz radiation only in a focal plane.

Multiple Illumination Angles

A challenge of imaging objects in the microwave or terahertz spectrum is the specular nature of reflections off of surfaces with features sizes that are smaller than the illumination wavelength. Unless corrective measures are taken, this leads to images with so-called "stealth regions" (e.g., gaps, blind-spots, or invisible objects).

In illustrative implementations of this invention, the problem of stealth regions is corrected or reduced by illuminating the scene with radiation from multiple transmitters positioned at different angles relative to the scene being imaged. Thus, the scene is illuminated with microwave or terahertz radiation from multiple angles. In some implementations, the transmitters emit radiation sequentially, one transmitter at a time, while one or more antennas sample data at the focal region.

In some implementations, sampled data regarding radiation from the multiple illumination angles is processed in order to reduce stealth regions, as follows: Multiple data cubes are captured, each for a different transmitter (and thus for a different illumination position). For example, in some cases, each scan results in a data-cube whose axes are angle in the horizontal direction, angle in the elevation direction, and radiation time-of-flight in the third dimension. The data cubes are corrected for projection geometry so that reflections in each data cube are aligned with a voxelized Cartesian space of the scene. A computer then performs an algorithm that "fuses" the data cubes by finding the maximum measured amplitude (or intensity) of the scattered reflection at each voxel.

In some implementations, computers perform more elaborate processing of multi-illumination data to recover even more information from the scene, such as the alignment of the surface-normals and improved 3D reconstructions. For example, a computer may extract, from measurements of radiation from multiple radiation sources, surface normal orientation in the scene to improve 3D reconstruction. Furthermore, a computer may determine, based on the dependency of the reflectivity of a scene on the illumination wavelength and incoming angle of radiation, material properties of objects in the scene.

In illustrative implementations of this invention: (a) the data for each illumination source may be captured at a different time than the other illumination sources, and (b) it is desirable that the scene be static during the acquisition process. However, the acquisition time may be so short that many different illuminations may occur in a short time period. (For example, acquisition may be shorter than 100 milliseconds, many illuminations can occur within 1 second). The imaging system may capture a data cube for each illumination. The data cube may represent a 3D volume in front of the camera, and may be voxelized so that X represents left and right, Z represents up and down, and Y represents forward and back from the camera.

In illustrative implementations, stealth regions (that would otherwise appear in an image produced from the data recorded by the imaging system) may be reduced by combining multiple illumination data-cubes. Stealth regions tend to be caused by certain illumination angles causing glancing reflections. Thus, by taking the maximum of multiple data-cubes with varying illumination angles, the chances of a region disappearing are reduced.

In illustrative implementations, a computer may take as input a fused-data-cube, and output signals that cause an I/O device to produce an interactive volumetric display, in which the fused-data-cube may be viewed volumetrically by viewing across individual vertical or horizontal slices. Furthermore, a computer: (a) may sum or take the maximum of voxels along the depth axis of fused-data-cube, (b) may calculate a 2D projection of the 3D dataset which shows a silhouette of the microwave scattering surfaces in the scene, and (c) may cause an I/O device to display the silhouette.

In some implementations of this invention, the imaging system determines the reflecting angle of the scattering surface by performing a photometric-stereo technique. This computational photography technique uses the diversity in the strength of reflection from multiple illumination angles to solve for the 3D orientation of the scattering surface at that pixel. Scattering shape and material properties at each pixel may also be estimated from the spectral response at each pixel. This spectral response shows the strength of reflection at each pixel across many wavelengths. Different materials and resonance shapes may appear to have different spectral responses. For example, a set of wire-resonators of varying length may appear, in images captured by the imaging system, to have varying spectral responses.

Multispectral Imaging

In illustrative implementations of this invention: (a) the microwave or terahertz transmitters emit radiation that varies in frequency over time, such as radiation chirps in which frequency increases linearly over time or decreases linearly over time; (b) one or more antennas located at the focal plane sample the multi-spectral radiation after it reflects from a near-field object and is focused by the passive aperture on the focal plane; and (c) one or more computers generate multi-spectral images from data indicative of these samples.

Advantageously, in illustrative implementations, multi-spectral imaging gathers more data that would be obtained from monochromatic imaging. In some cases, this is due to: (a) varying point spread function (PSF) at different radiation frequencies, and (b) varying reflectance properties at different radiation frequencies. For example, reflectance lobes tend to be wider at short wavelengths than at longer wavelengths. Also, shorter objects tend to reflect only shorter wavelengths, if the dimension of the object is of resonant length (or in other words, this dimension is such that it causes the object to resonate thereby scattering greater energy at some wavelength(s) more than others) within the bandwidth of wavelengths being emitted by the transmitters.

In illustrative implementations, a computer classifies materials in scenes, by analyzing data indicative of multi-spectral microwave or terahertz radiation that reflected from a near field object and traveled to the imaging system.

Figure 2A:
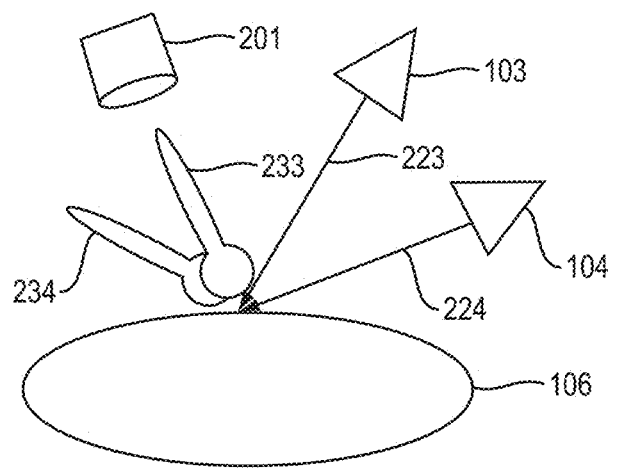
FIGS. 2A and 2B are conceptual diagrams that show that reflectance nodes for short wavelengths are wider than those for long wavelengths.
Figure 2B:
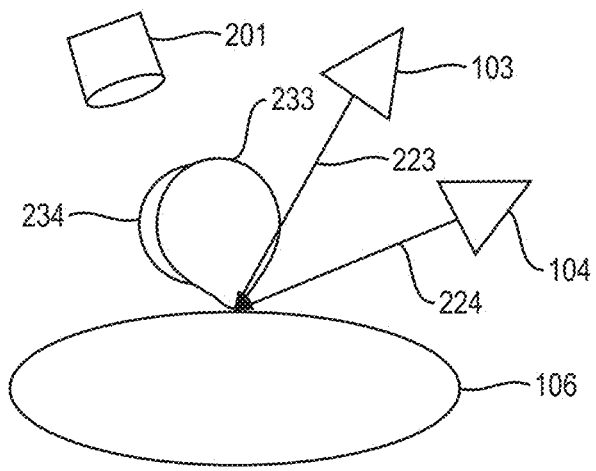

FIGS. 2A and 2B are conceptual diagrams that show that reflectance nodes for short wavelengths are wider than those for long wavelengths, in an illustrative implementation of this invention.

In FIGS. 2A and 2B, a microwave or terahertz imaging system includes two transmitters 103, 104 and a sensor 201. The sensor 201 includes (i) a passive aperture (e.g., a parabolic reflector or dielectric lens) for focusing radiation onto a focal plane and (ii) one or more antennas for sampling radiation at the focal plane.

In FIGS. 2A and 2B: (a) transmitter 103 emits radiation that includes ray 223, which reflects off of object 106 to form reflectance node 233, and (b) transmitter 104 emits radiation that includes ray 224, which reflects off of object 106 to form reflectance node 234.

The wavelength of radiation emitted by transmitters 103, 104 in FIG. 2B is shorter than in FIG. 2B. Thus, reflectance lobes 233, 234 are wider in FIG. 2B than in FIG. 2A.

Figure 3:
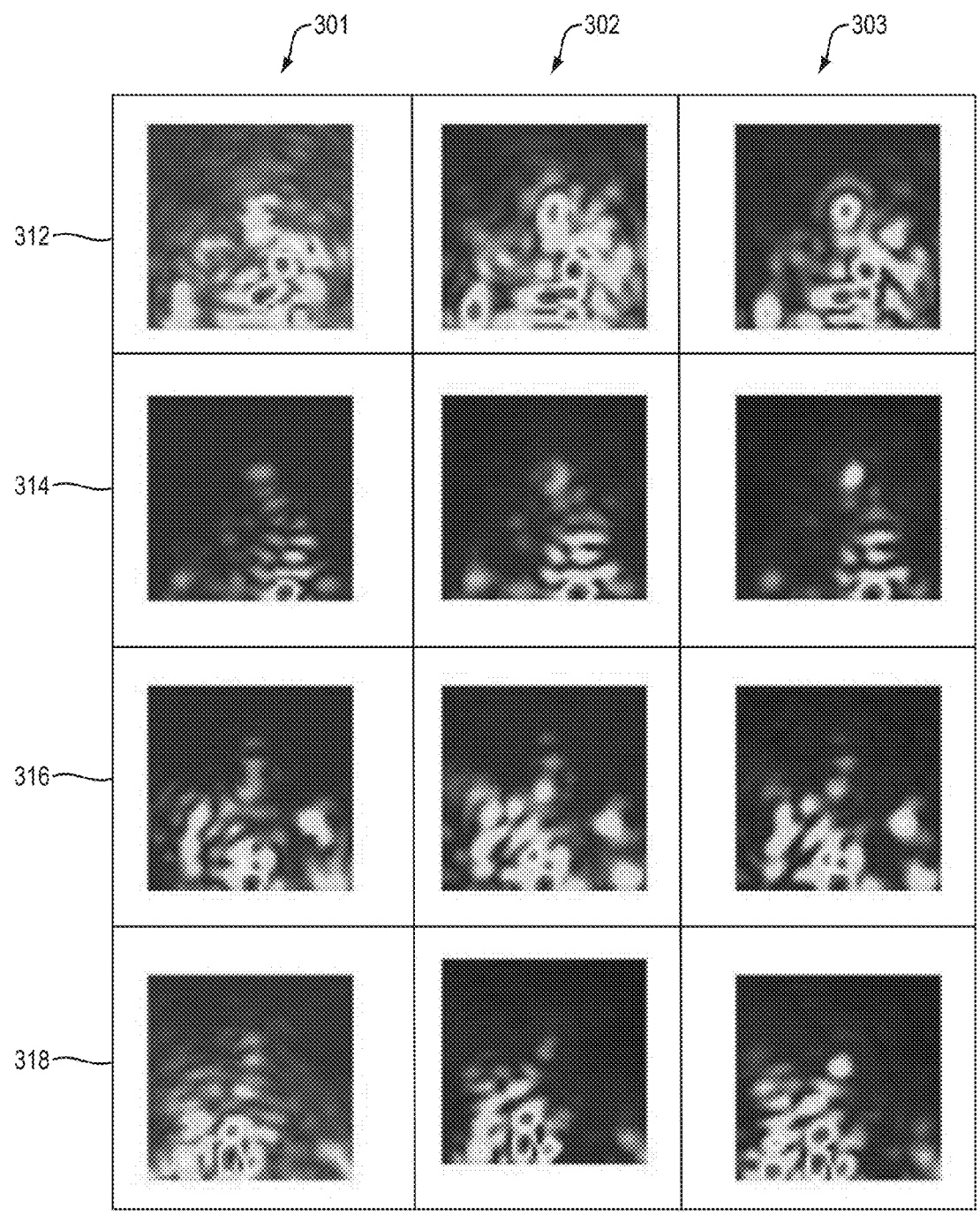
FIG. 3 is a set of twelve images of a mannequin captured under microwave illumination.

FIG. 3 is a set of twelve images of a mannequin captured under microwave illumination, in an illustrative implementation of this invention. For each horizontal row of FIG. 3, the three images in that row were created by breaking down a single image into three images that correspond to energy received in different spectral bands of microwave radiation. Specifically, in each horizontal row of FIG. 3: (a) the image on the left shows intensity of radiation received in a spectral band of longer wavelengths, (b) the image in the middle column shows intensity of radiation received in a middle spectral band, and (c) the image on the right shows intensity of radiation received in a spectral band of shorter wavelengths.

In FIG. 3, the three different spectral bands lead to diversity in reflectance properties, thereby capturing more information about the mannequin being imaged. Among other things, the reflectance lobes for short wavelengths are wider than the reflectance lobes at long wavelengths, thus the multi-spectral images of the mannequin provide additional information depending on the size of features in the scene.

In FIG. 3, each different horizontal row consists of an image (broken into three images that show three spectral bandwidths) taken under illumination from a different transmitter antenna. Specifically, horizontal rows 312, 314, 316, 318 show images that were captured under illumination from a first transmitter, second transmitter, third transmitter and fourth transmitter, respectively. As noted above, the vertical columns 301, 302, 303 correspond to different spectral bands.

In illustrative implementations of this invention, a microwave or terahertz imaging system: (a) performs 3D imaging with spatially-independent spectral information; and (b) breaks down an image by its spectral information at no loss of spatial resolution. The imaging system has multi-spectral capabilities while still providing depth, 3D shape, and a reduced number of sensor elements.

Imaging Through a Partition

In illustrative implementations of this invention, a microwave or terahertz imaging system images through a partition (such as dry-wall, plywood or ceramic) that is opaque to visible light. The imaging system is able to do so because many common materials are transparent, or have low reflectivity, under microwave or terahertz radiation.

In some implementations, the reflection (in the microwave or terahertz frequency band) from the target near-field object is much stronger than the reflection from the partition. Furthermore, in some cases, reflections from the partition are ignored by (a) capturing a time-of-flight movie (in which different frames correspond to the arrival of radiation that has traveled different roundtrip distances from the transmitter to the scene and back to the receiving antennas) and (b) ignoring the frames in which the reflection from the partition occurs.

The ability to image through partitions (such as the wall of a cardboard packing box) has many practical advantages. For example, imaging through a partition may be employed for nondestructive testing or evaluation of an object in a container in order to ensure its structural health or topology.

Figure 4:
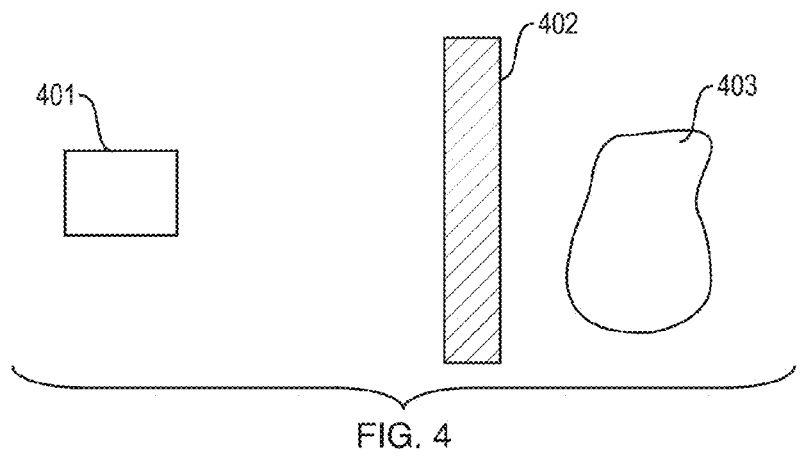
FIG. 4 is a diagram that shows a microwave or terahertz imaging system for imaging an object through a partition that is opaque to visible light.

FIG. 4 is a diagram that shows a microwave or terahertz imaging system, in an illustrative implementation of this invention. The imaging system 401 images an object 403 through a partition 402 that is opaque to visible light.

Prototype

The following twenty-three paragraphs are a description of a prototype of this invention:

In this prototype, the imaging system operates in the microwave X-band region (8-12 GHz) of the electromagnetic spectrum using a frequency-modulated continuous-wave (FMCW) transmitter and receiver.

In this prototype, the transmitter is re-locatable and enables the scene to be illuminated from arbitrary locations. Near-field objects in the scene reflect the transmitted waves, which are then collected and focused by a parabolic dish onto the focal plane. The parabolic reflector has a diameter of 1.22 m and a focal length of 0.45 m. A sensor is raster scanned in X and Y through the focal plane and a 41 pixel×41 pixel image is captured over a 25.4 cm by 25.4 cm area. At each measurement point, the emitter is linearly swept from 7.835 GHz to 12.817 GHz over a 10 ms period, and the received signal is demodulated by mixing the received signal with the transmitted signal and then applying a low pass filter. The amplitude of the demodulated signal is sampled at 200 kHz using an analog-to-digital converter. The imaging system is calibrated by measuring the response of an aluminum sphere placed in front of the system. The scanning system and receiving element supports are covered in radar absorbing material to minimize interference effects, furthermore they are outside of the depth of field of the camera. Each scan leads to a data-cube whose axes are angle in the horizontal direction, angle in the elevation direction, and the microwave time-of-flight in the third dimension. Time-of-flight data is computed based upon FMCW radar processing.

This prototype has a Rayleigh-limited resolution of 200 ps, thus facilitating visualization of physical electromagnetic phenomena such as pulse reflections of microwave energy as a function of time propagating through an image.

In this prototype, a transmitting antenna illuminates the scene. Specifically, an ultra-wideband (UWB) antenna emits a continuous wave (CW) in which the frequency is linearly swept from 7.835~GHz to 12.817~GHz, for a bandwidth, BW, of 4.982 GHz, over a chirp width, $T_p$, of 10 ms. This is represented by $$TX(t) = \cos\left(2\pi\left(f_{osc} + \frac{c_r}{2}t\right)t\right)$$

where $f_{osc}$ is the start frequency of the linear-ramp modulated voltage controlled oscillator (VCO) and $c_r$ is equal to the radar chirp rate $BW/T_p$.

In this prototype, scattered microwaves are collected and focused by a lens-equivalent parabolic reflector of radius r, where radius r is the radius of the largest circle formed by the dish of the reflector. In this prototype, the parabolic reflector is shaped such that it focuses collimated radiation from a distant source to a focal point which is located at a distance $f_{far}=r/2$ from the vertex of the parabola.

In this prototype, the target scene is in the near-field of the parabolic reflector. Radiation reflecting from a near-field object is focused onto a focal plane, which focal plane is perpendicular to the axis of symmetry of the parabolic reflector and is at a distance d from the vertex of the parabolic reflector. In this prototype, this distance d is such that $r/2<d\leq r$.

In this prototype, using a parabolic reflector is less expensive and less difficult to mount than using an equivalently sized dielectric lens.

In this prototype, an X band (WR-90) waveguide probe is mounted to an X-Y translation stage and is moved to different points to sample the incident microwave radiation over the image plane. Scattered and focused signals are collected by this waveguide probe and are represented by (without loss of generality, ignoring amplitude coefficients)

$$RX(t)=TX(t-t\_\{delay\})$$

where roundtrip time $t_{delay}$ is the time taken to reach and scatter off of the target, return to and be focused by the dish, and be collected by the waveguide probe.

In this prototype, the probe signal is fed into the receive port of a UWB frequency-modulated continuous-wave (FMCW) receiver. The received delayed FMCW signal from the waveguide probe is then amplified by a low-noise amplifier then fed into a frequency mixer. The illumination chirp is also fed into the frequency mixer multiplies the sampled chirp by the reflected chirp, $m(t)=TX(t)\cdot TX(t-t_{delay})$ This product is amplified by the video amplifier and then digitized. This analog signal is digitized at a rate of 200 kHz.

In this prototype, the high frequency term of this cosine multiplication is rejected by the low-pass filter within the video amplifier resulting in $$V(t)=\cos(2\pi c_r f_{osc} t_{delay} t+\phi)$$

In this prototype, when there is only one target present V(t) is a sinusoidal wave with frequency proportional to $t_{delay}$; if multiple targets are present then V(t) is a superposition of numerous sinusoids, each with frequencies proportional to the round-trip delay to its corresponding reflector.

In this prototype, a cube of data (angle, angle, time) is acquired using an X-Y translation stage where a 41 pixel by 41 pixel image is sampled. At each position 2000 analog samples are acquired and synchronized to the chirp time, $T_p$. This results in the signal $V(x_n,y_n,t)$, where $x_n$ and $y_n$ are the horizontal and vertical positions, respectively, of the waveguide probe (i.e., the receiving antenna) in the 2D detector sampling plane.

In this prototype, to process and generate a microwave image, the time-average intensity of the entire signal V(t) is computed for each pixel $x_n$ and $y_n$, resulting in the image $s_{image}(x_n,y_n)$.

In this prototype, the imaging system does not capture all pixels simultaneously like a film camera; instead it captures pixels sequentially in time using a scanning waveguide.

In this prototype, the system's frequency response may be calibrated as follows: Data may be acquired regarding a baseline target which is an aluminum sphere placed in front of the imaging system. Background subtraction may be performed. This measurement with the sphere may be compared with the Mie series solution for an ideal sphere of the same size. The system phase and frequency response may be calibrated by dividing the Mie data cube $S_{Mie}$ by the calibration image $S_{cal}$ $$S_{cf}(V(t)) = \frac{S_{Mie}(V(t))}{S_{cal}(V(t))}$$

In this prototype, to apply calibration, each sample over V(t) in the data cube is multiplied by the calibration factor $S_{cf}$, resulting in the calibrated data cube $S_{calibrated}(x_n,y_n,V(t))$.

In this prototype, the spatial frequency domain data cube is divided up evenly into three sub-bands over V(t) of 666 samples each. These bands are color coded as so-called "red", "green", and "blue" with mean center frequencies of "red" (8.66~GHz), "green" (10.32~GHz), and "blue" (11.97~GHz) respectively. To do this, $s(x_n,y_n,V(t))$ becomes $s_{red}(x_n,y_n,V_{red}(t))$, $s_{green}(x_n,y_n,V_{green}(t))$, and $s_{blue}(x_n,y_n,V_{blue}(t))$. A DFT is applied to each sub-band in order to provide the range domain response of each color. The imagery is displayed in both range and color.

In this prototype, since FMCW processing uses system bandwidth to determine depth, each spectral division reduces the range domain resolution of the system. The reduction in range domain resolution is linearly related to the number of sub-bands desired in the final image.

In this prototype, an additional calibration step is taken when imaging in multi-spectral mode, white balance. White balance is achieved by imaging a relatively large (i.e. compared to a wavelength) sphere and scaling all color bands to the same amplitude as the center of the image. White balance is similarly applied to all multi-spectral imagery thereafter.

This prototype over samples the diffraction-limited image.

In this prototype, the focal plane of a simple passive reflector is sampled. This allows a trade-off, in which increased field-of-view (FOV) is traded for a reduction in the number of measurements for imaging dense scenes.

In this prototype, the imaging system achieves 0.5 degree resolution. By limiting the field of view to objects in front of the imaging system, this prototype uses only 1,681 measurements (fewer than ¼th of the measurements required for an equivalent phased array) while imaging at the same resolution.

In this prototype, the imaging system has a temporal resolution of substantially 200 picoseconds and a depth resolution of substantially 6 cm.

This invention is not limited to the prototype described in the preceding twenty-three paragraphs. Instead, this invention may be implemented in many different ways.

Scanning Receiver Antenna

In some implementations of this invention, a passive aperture (e.g., parabolic reflector or dielectric lens) focuses light onto a region of a focal plane, and actuators mechanically scan a receiver antenna—i.e., move the receiver antenna to different points in this region. In this approach, the entire region is not sampled simultaneously. Instead, the receiver antenna samples incident radiation at different points of the region at different times, as the receiver antenna sequentially scans the region.

Figure 5A:
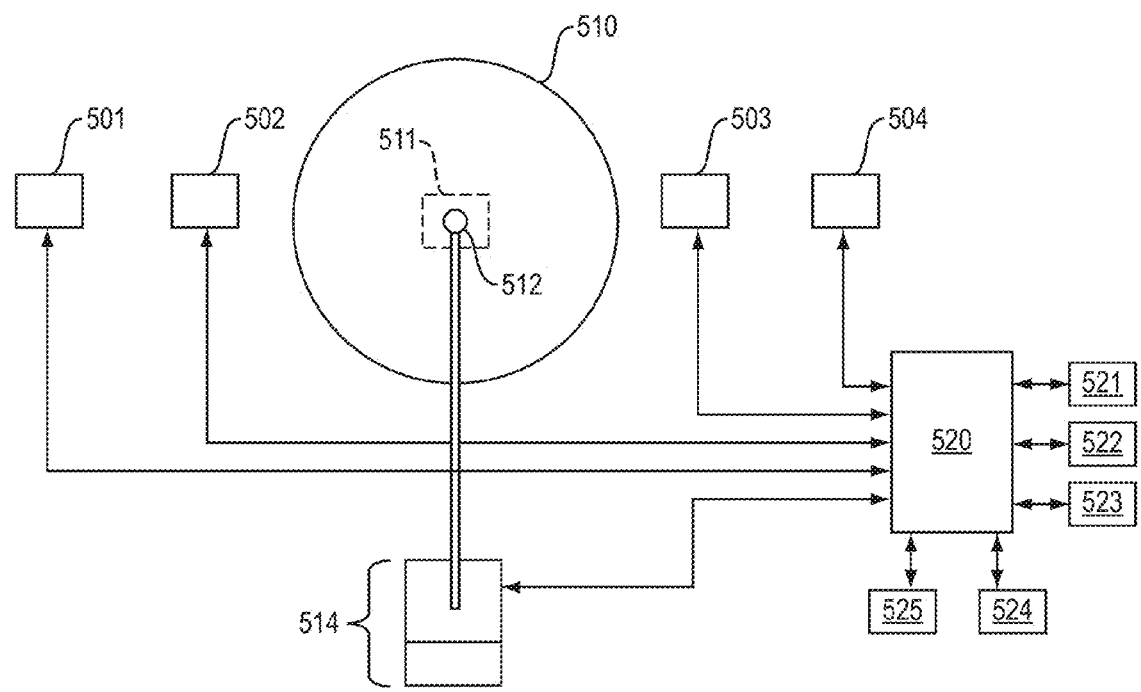
FIGS. 5A and 5B show a microwave or terahertz imaging system that employs a scanning receiver antenna and a parabolic reflector.
Figure 5B:
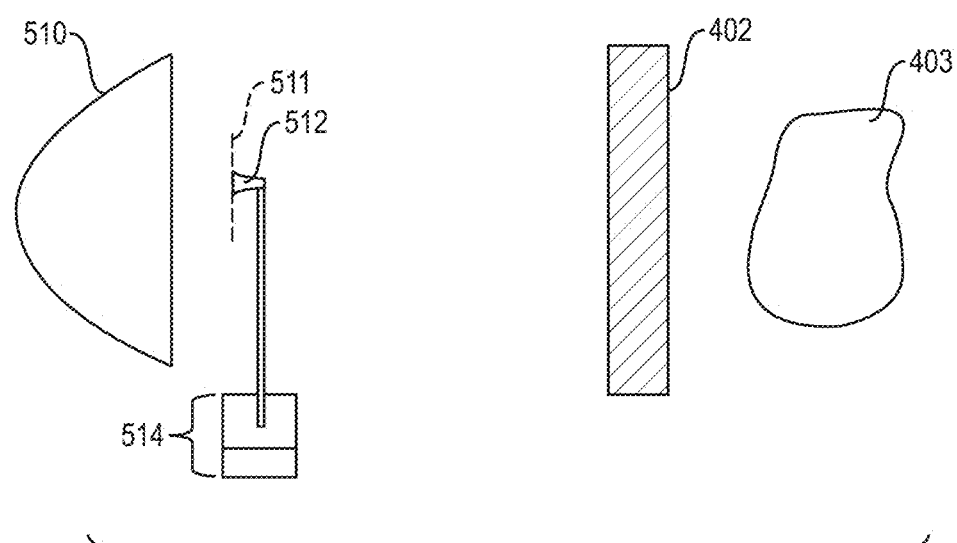

FIGS. 5A and 5B show a microwave or terahertz imaging system that employs a scanning receiver antenna and a parabolic reflector, in an illustrative implementation of this invention. FIG. 5A is a front view of the system; FIG. 5B is a side view of the system.

In the example shown in FIGS. 5A and 5B, multiple transmitter antennas 501, 502, 503, 504 emit microwave or terahertz radiation that reflects from a near-field object and then travels to a parabolic reflector 510. The parabolic reflector 510 focuses this radiation onto a region of a focal plane 511. Actuators 514 translate a receiver antenna 512 (e.g., a horn antenna) to different points in this region in order to sample the incident radiation in this region sequentially, one point at a time. One or more computers (e.g. 520) control the transmitter antennas 501, 502, 503, 504 and the actuators 514. The one or more computers (e.g., 520) process data gathered by the receiver antenna 512, including to produce images (or other data representations) that convey information regarding the 2D brightness, depth, and multi-spectral response of a near-field object that is being imaged.

In FIGS. 5A, 5B, 6A and 6B, the one or more computers (e.g., 520) interface with multiple I/O devices, including a display screen 521, keyboard 522, microphone 523, and speaker 524. The one or more computers read data from, and write data to, a memory device 525.

In FIG. 5B, the imaging system (including reflector 510 and antenna 512) may image a near-field object 403. In some use scenarios, this imaging may be performed through a solid partition 402 that is opaque to visible light. Antenna 512 may be any shape. For example, antenna 512 may be a horn antenna. Or, for example, antenna 512 may be a "sawed-off" rectangular waveguide that provides the smallest-possible aperture pixel for that waveguide.

Figure 5C:
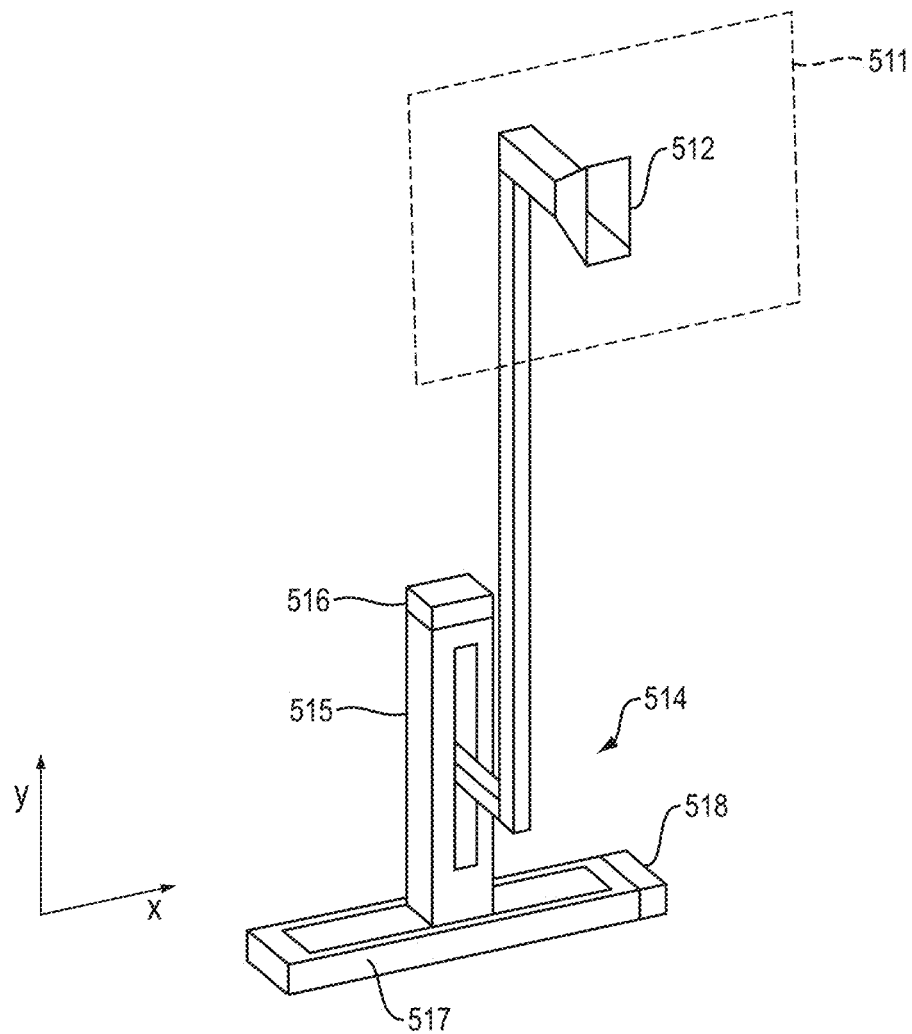
FIG. 5C is a perspective view of a scanning receiver antenna and of actuators for moving the antenna to different points in a focal plane.

FIG. 5C is a perspective view of a scanning receiver antenna 512 and of actuators for moving the antenna to different points in a focal plane 511, in an illustrative implementation of this invention. The actuators include an x-axis stepper motor 518, an x-axis translation rail 517 for guiding movement along the x-axis, a y-axis stepper motor 516, and a y-axis translation rail 515 for guiding movement along the y-axis.

Figure 5D:
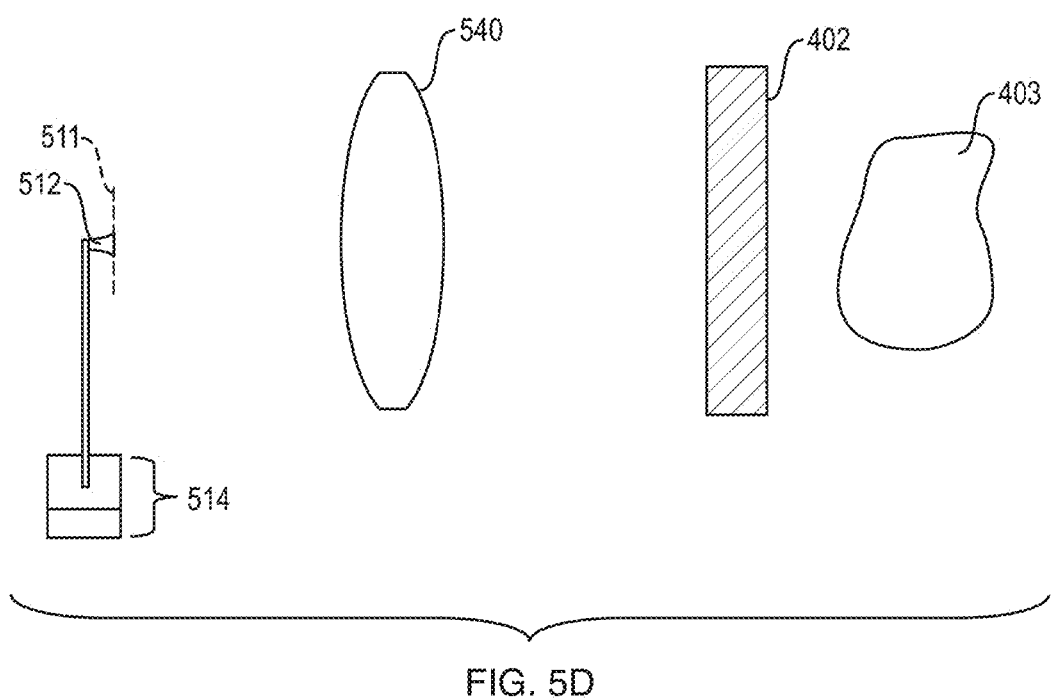
FIG. 5D is a side view of a microwave or terahertz imaging system that employs a scanning receiver antenna and a dielectric lens.

FIG. 5D is a side view of a microwave or terahertz imaging system that employs a scanning receiver antenna 512 and a dielectric lens 540, in an illustrative implementation of this invention.

In the setup shown in FIG. 5D, transmitter antennas emit microwave or terahertz radiation that illuminates a near-field object 403. This radiation then reflects from object 403 and travels to dielectric lens 540. The dielectric lens 540 focuses the radiation onto focal plane 511. Actuators 514 translate the receiver antenna 512 to different points in this region in order to sample the incident radiation in this region sequentially, one point at a time. In some use scenarios, this imaging may be performed through a solid partition 402 that is opaque to visible light.

In some implementations of this invention (e.g., in the examples shown in FIGS. 5A, 5B, 5C and 5D), a phase center of antenna 512 may be located at, or positioned in, focal plane 511 during sampling of the radiation.

Wavelength and Size of Passive Aperture

This invention may employ radiation in the microwave or terahertz frequency band.

In some implementations, it is desirable to reduce the size of the passive aperture (e.g., parabolic reflector or dielectric lens) by reducing the wavelength of radiation that is employed.

In some cases, it is desirable for the maximum dimension of the aperture to be substantially equal to a given number of wavelengths of the longest wavelength of radiation that is employed by the imaging system. For example, the inventors found, in tests of a prototype of this invention, that using a passive aperture with a maximum diameter that is substantially equal to 50 wavelengths resulted in good angular resolution.

The size of the passive aperture that is needed (in order for the maximum dimension of the passive aperture to be equal to a given number of wavelengths of the imaging radiation) varies depending on the wavelength of the imaging radiation. The higher the frequency, the shorter the wavelength, and thus the smaller the passive aperture that is needed.

For example, in order to achieve an aperture that has a maximum dimension that is equal to a given number of wavelengths, a much smaller aperture could be employed for 3 THz terahertz radiation with a wavelength of 0.1 millimeters than for 300 MHz microwave radiation with a wavelength of 1000 millimeters: specifically, the aperture could be 10,000 times smaller for the latter than for the former.

Also, for example, in order to achieve an aperture that has a maximum dimension that is equal to a given number of wavelengths, a much smaller aperture could be employed for microwave radiation with a wavelength of 9 cm than for microwave radiation with a wavelength of 3 mm: specifically, the aperture could be 30 times smaller for the latter than for the former.

In some implementations, employing a dielectric lens becomes more practical, cost-effective and desirable as the wavelength of imaging radiation decreases. This is because the size of the dielectric lens tends to decrease as the wavelength decreases.

Advantageously, this invention may be miniaturized by reducing the radiation wavelength—e.g., to the millimeter-wave band of microwave or to the terahertz band.

Furthermore, in some implementations of this invention, a smaller wavelength of radiation and smaller aperture (e.g. dielectric lens) makes the imaging system smaller, and thus make it well-suited for numerous applications, including as an imaging device mounted on an autonomous car.

In some implementations of this invention, the microwave or terahertz imaging system is deployed on an autonomous vehicle and produces, in real time, highly useful data regarding the vehicle's surroundings, including 2D images, depth data, classification of material properties of near-field objects and other data useful for steering and controlling the autonomous vehicle. An advantage of microwave or terahertz radiation is that it can image through fog, drizzle or rain, unlike LIDAR imaging systems. The ability to image through fog, drizzle or rain is desirable for autonomous vehicles.

Dielectric Lens

In some implementations of this invention, the passive aperture (which focuses the microwave or terahertz radiation onto a focal plane) comprises a dielectric lens (e.g., 540, 801). For example, the dielectric lens (e.g., 540, 801) may comprise one or more of the following materials: (i) ABS (acrylonitrile butadiene styrene), (ii) ABS-M30, (iii) acrylic glass, (iv) alumina, (v) fused quartz, (vi) fluorphlogopite mica in borosilicate glass (e.g., MACOR®), (vii) polyethylene, (viii) polypropylene, (ix) polysterene, (x) polytetrafluoroethylene (e.g., Teflon) (xi) compressed foam, (xii) silicon, (xiii) gallium arsenide, or (xiv) a metamaterial (e.g., a metamaterial with a negative dielectric constant). For example, in some cases, the dielectric lens (e.g., 540, 801) may comprise one or more materials that each have a dielectric constant, when exposed to 30 GHz radiation, that is between 1.1 and 100, or that is less than 0.9.

In some cases, the dielectric lens has axial symmetry. In some cases, the dielectric lens has an air-filled cavity or depression. In some cases, the dielectric lens has relative permittivity that is anisotropic. In other cases, the dielectric lens has relative permittivity that is isotropic. The dielectric lens (e.g., 540, 801) may comprise a single lens, compound lens or lens system.

Sensor Array at Focal Plane

In some implementations of this invention, real-time imaging with microwave or terahertz radiation is achieved by using an "on-chip" sensor array that employs multiple antennas to sample the radiation at multiple points of a focal plane simultaneously.

In other implementations of this invention, real-time imaging with microwave or terahertz radiation is achieved by using a reconfigurable sensor to sample radiation at the focal plane.

Figure 6A:
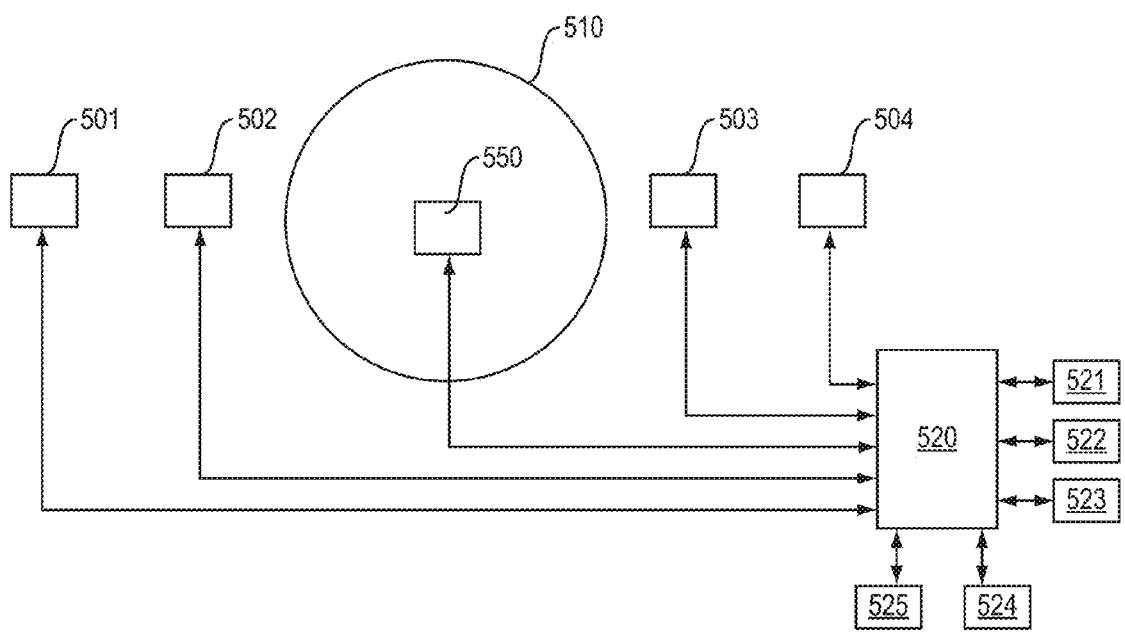
FIGS. 6A and 6B show a microwave or terahertz imaging system that includes a parabolic reflector and a sensor array for measuring radiation in a focal plane.
Figure 6B:
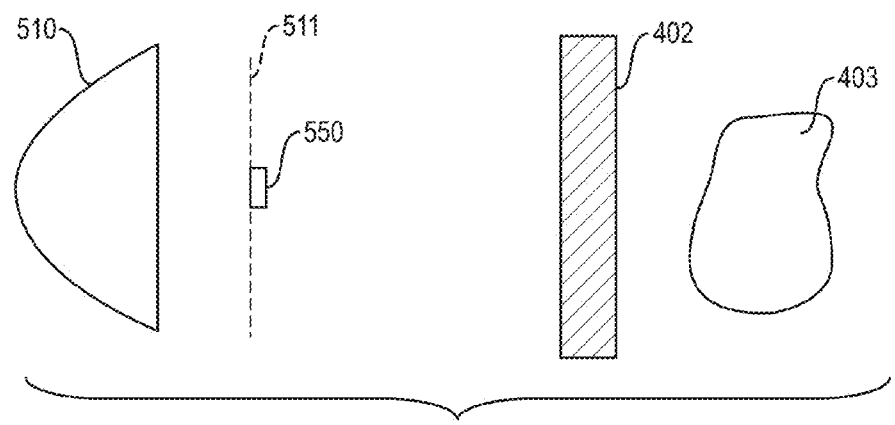

FIGS. 6A and 6B show a microwave or terahertz imaging system that includes a parabolic reflector 510 and a sensor array 550 for measuring radiation in a focal plane, in an illustrative implementation of this invention. FIG. 6A is a front view of the system; FIG. 6B is a side view of the system.

The system shown in FIGS. 6A and 6B is similar to that shown in FIGS. 5A and 5B, except that a sensor array 550 replaces the actuators 514 and scanning antenna 512.

In the example shown in FIGS. 6A and 6B, multiple transmitter antennas 501, 502, 503, 504 emit microwave or terahertz radiation that reflects from a near-field object and then travels to a parabolic reflector 510. The parabolic reflector 510 focuses this radiation onto a focal plane.

In FIGS. 6A and 6B, a sensor array 550 samples the focused radiation at multiple points in the focal plane. For example, sensor array 550 may comprise an "on-chip" CMOS sensor array which includes multiple antennas that (a) are located at the focal plane and (b) taken together, sample multiple points of the focal plane simultaneously. Alternatively, sensor array 550 may comprise a reconfigurable sensor located at the focal plane.

In FIGS. 6A and 6B, one or more computers (e.g. 520) control the transmitter antennas 501, 502, 503, 504. The one or more computers (e.g., 520) also process data gathered by the sensor array 550, including to produce images (or other data representations) that convey information regarding the 2D brightness, depth, and multi-spectral response of a near-field object that is being imaged.

In FIG. 6B, the imaging system (including reflector 510 and sensor array 550) may image a near-field object 403. In some use scenarios, this imaging may be performed through a solid partition 402 that is opaque to visible light.

Figure 6C:
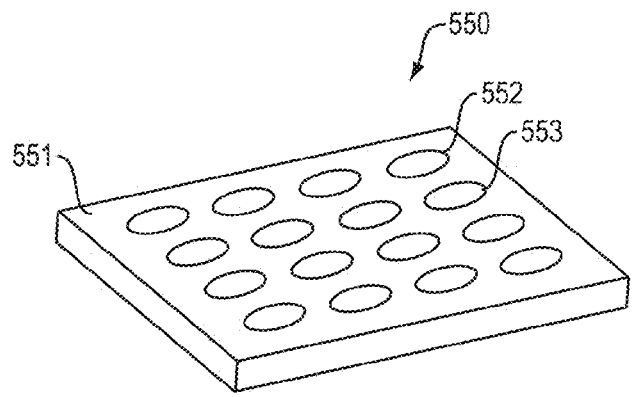
FIGS. 6C and 6D each show an "on-chip" sensor array for measuring microwave or terahertz radiation in a focal plane.
Figure 6D:
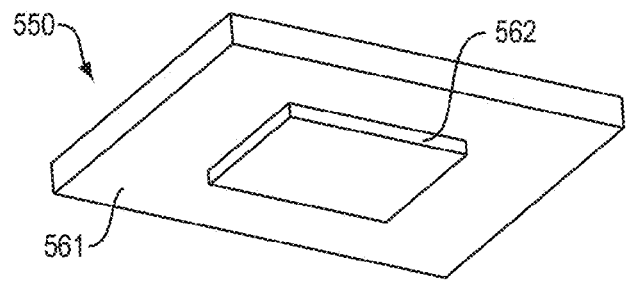

FIGS. 6C and 6D show an "on-chip" CMOS sensor array 550 for measuring microwave or terahertz radiation in a focal plane, in an illustrative implementation of this invention. In FIG. 6C, the front side 551 of the "on-chip" sensor array is visible. Multiple antennas (e.g., 552, 553) are located on the front, scene-facing side of the sensor array 550. These multiple antennas simultaneously sample microwave or terahertz radiation at multiple points of a focal plane. In some cases, a subset of the multiple antennas emits microwave or terahertz radiation and another subset of the multiple antennas measure the radiation after it reflects back from the scene. In FIG. 6D, the back side 561 of the "on-chip" sensor array 550 is visible, including a CMOS integrated circuit 562.

Figure 6E:
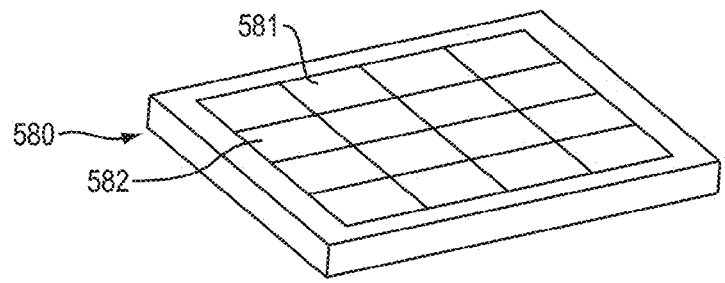
FIGS. 6E and 6F each show a reconfigurable sensor array for measuring microwave or terahertz radiation in a focal plane.
Figure 6F:
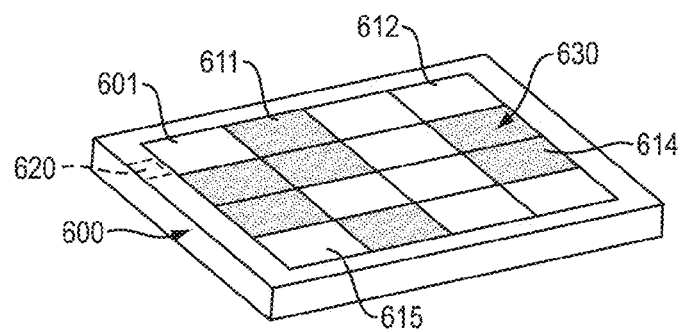

FIGS. 6E and 6F each show a reconfigurable sensor array for measuring microwave or terahertz radiation in a focal plane, in illustrative implementations of this invention.

In FIG. 6E, a reconfigurable sensor array 580 includes switchable antennas (e.g., 581, 582).

In FIG. 6F, a reconfigurable sensor array 600 includes a programmable mask 630. The mask 630 includes multiple pixels (e.g., 601, 611, 612, 614, 615) whose transparency (or inversely, opacity) is controllable by a computer (e.g., 620). The degree of transparency of each pixel may be controlled in a binary fashion (on/off) or in multiple gradations. FIG. 6F shows the mask 630 at a time in which certain pixels (e.g., 611, 614) are "off" (i.e., not allowing radiation to pass through them) and in which other pixels (e.g., 612, 615) are "on" (i.e., allowing radiation to pass through them).

In some implementations, a computer processes data obtained by the reconfigurable sensor, by performing a compressive sensing algorithm or sparse recovery algorithm.

Figure 6G:
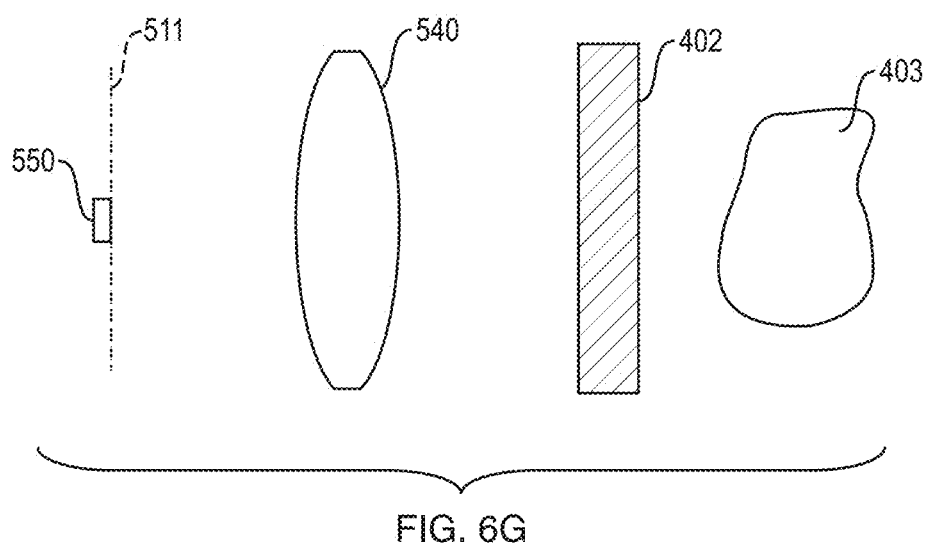
FIG. 6G is a side view of a microwave or terahertz imaging system that employs a sensor array and a dielectric lens.

FIG. 6G is a side view of a microwave or terahertz imaging system imaging a near-field object, in an illustrative implementation of this invention. The imaging system employs a sensor array 550 and a dielectric lens 540. The lens 540 focuses radiation from near-field object 403 onto focal plane 511. In some use scenarios, this imaging may be performed through a solid partition 402 that is opaque to visible light.

In some implementations of this invention (including examples shown in FIGS. 6A, 6B, 6B, 6C, 6E, 6F and 6G): (a) sensor array (e.g. 550, 580 or 600) may include a set of one or more antennas for measuring radiation; and (b) a phase center of at least one antenna in the set may be located at, or positioned in, focal plane 511.

More Details

Figure 7:
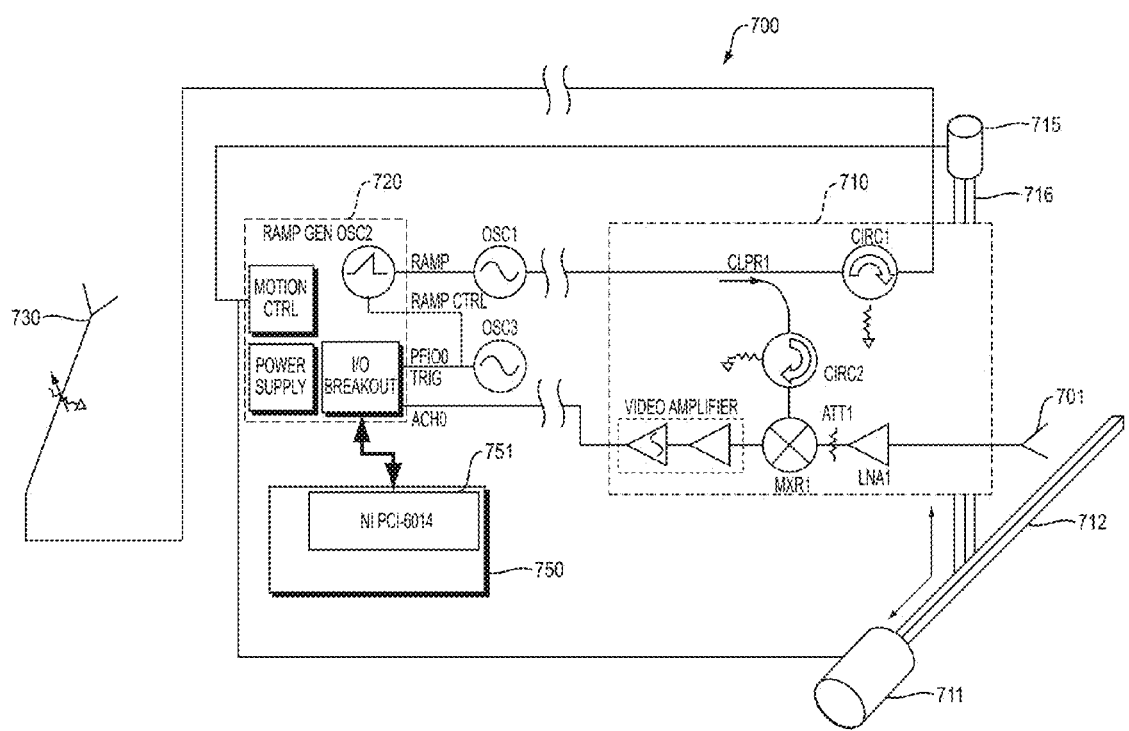
FIG. 7 is a diagram of a microwave or terahertz imaging system that includes actuators for mechanically scanning an antenna in a focal plane.

FIG. 7 is a diagram of a microwave or terahertz imaging system 700 that includes actuators for mechanically scanning an antenna in a focal plane, in an illustrative implementation of this invention. In FIG. 7, actuators for scanning a receiver antenna (waveguide probe) 701 in a focal plane include (a) an x-axis stepper motor 715 that actuates an x-axis linear stage 716, and (b) a y-axis stepper motor 711 that actuates a y-axis linear stage 712.

In the example shown in FIG. 7, a radar front end 710 interfaces with both receiver antenna 701 and one or more transmitter antennas (e.g., antenna 730). In the radar front end 710, the probe signal from the receiver antenna 701 is fed into the receive port of a UWB frequency-modulated continuous-wave (FMCW) receiver. The received delayed FMCW signal from the receiver antenna is then amplified by a low-noise amplifier and then fed into a frequency mixer. The illumination chirp is also fed into the frequency mixer. The frequency mixer multiplies the sampled chirp by the reflected chirp. This product is amplified by the video amplifier.

In FIG. 7, a computer 750 controls and interfaces with a radar controller 720, which in turn controls and interfaces with the radar front end 710. The computer 750 includes a data acquisition board 751 (such as a National Instruments® NI PCI-6014 16-bit, 16 analog input multifunction data acquisition board).

Figure 8:
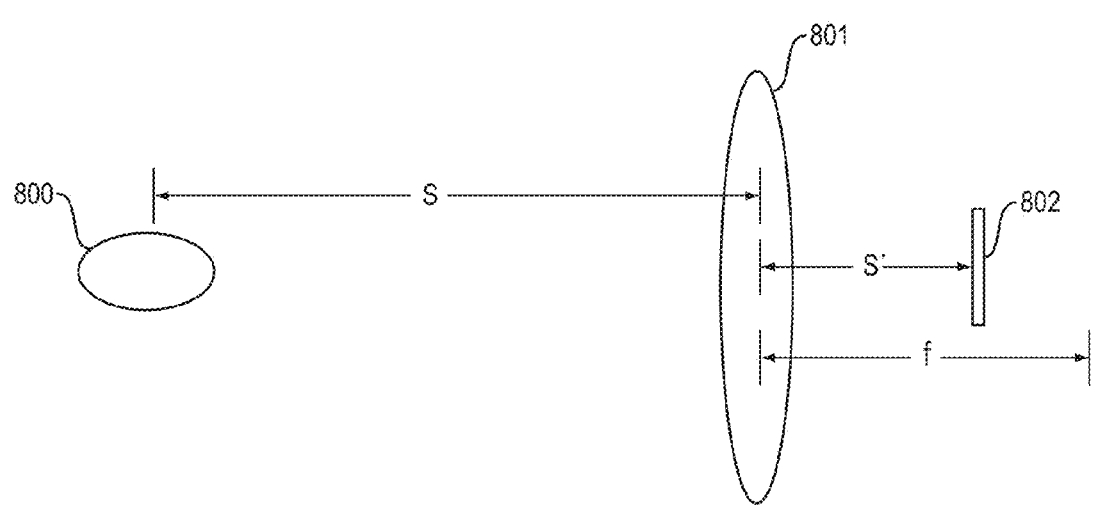
FIG. 8 is a diagram of a microwave or terahertz imaging system with a dielectric lens and sensor array for measuring microwave or terahertz radiation incident at a focal plane.

FIG. 8 is a diagram of a microwave or terahertz imaging system with a dielectric lens 801 and sensor array 802 for measuring microwave or terahertz radiation incident at a focal plane, in an illustrative implementation of this invention. In the example shown in FIG. 8, a dielectric lens 801 is located at distance s from a near-field object 800 that is being imaged. Microwave or terahertz radiation reflects from object 800 and is focused by dielectric lens 801 onto a focal plane. Sensor array 802 is located at this focal plane and is at distance s' from dielectric lens 801. According to a thin-lens approximation, the distances shown in FIG. 8 are related as follows:

$$\frac{1}{s} + \frac{1}{s'} = \frac{1}{f}$$

where f is the focal length of dielectric lens 801.

Figure 9:
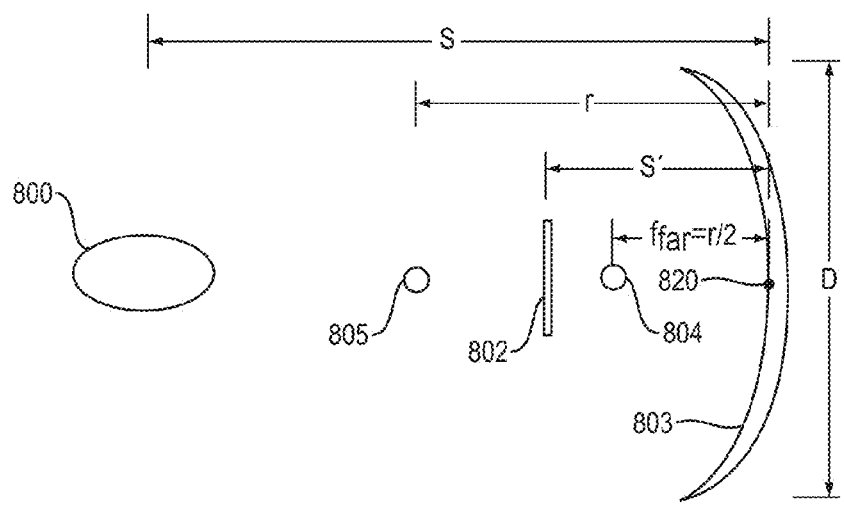
FIG. 9 is a diagram of a microwave or terahertz imaging system with a parabolic reflector and sensor array for measuring microwave or terahertz radiation incident at a focal plane.

FIG. 9 is a diagram of a microwave or terahertz imaging system with a parabolic reflector 803 and sensor array 802 for measuring microwave or terahertz radiation incident at a focal plane, in an illustrative implementation of this invention.

In the example shown in FIG. 9, the vertex 820 of the parabolic reflector 803 is located at distance s from a near-field object 800 that is being imaged. In FIG. 9, D and r are the diameter and radius, respectively, of the largest circle formed by the dish of the reflector 803. Put differently, D is the maximum dimension of the reflector 803. Microwave or terahertz radiation reflects from near-field object 800 and is focused by parabolic reflector 803 onto a focal plane. Sensor array 802 is located at this focal plane and is at distance s' from the vertex 820 of the parabolic reflector 803. The focal plane (and thus the sensor array) is between points 805 and 804. In the example shown in FIG. 9, points 805 and 804 are located at distances r and r/2, respectively, from the vertex 820 of the parabolic reflector 803. According to a thin-lens approximation, the distances shown in FIG. 9 are related as follows:

$$\frac{1}{s} + \frac{1}{s'} = \frac{1}{f}$$

where $f=f_{far}=r/2$, and where $f_{far}$ is the distance, from the vertex of the parabola, at which collimated radiation from a distant source is focused by the parabola.

In other cases, $f_{far}$ is not equal to r/2.

In some implementations of this invention: (a) the passive aperture comprises a parabolic reflector; and (b) the focal plane (at which the parabola focuses radiation from a near-field object) is positioned at a distance from the vertex of the parabola that is greater than $f_{far}$, regardless of whether $f_{far}=r/2$.

In illustrative implementations, a sensor array or scanning antenna samples focused radiation from a near-field object. For example: (a) if a scanning antenna is employed to sample radiation at the focal plane, a phase center of the scanning antenna may move to different points in a focal plane, or (b) if a set of one or more antennas in a sensor array is employed to sample radiation at the focal plane, a phase center of at least one antenna in the set may be located at the focal plane. In the preceding sentence, the focal plane is the plane onto which the passive aperture (e.g., a parabolic reflector or dielectric lens) focuses radiation from a near-field object being imaged. In illustrative implementations, this focal plane is not in the same location as the point at which collimated light from a far-field point source would be focused. (The same analysis applies, mutandis mutatis, if the passive aperture focuses the radiation onto a curved region). Thus, in many implementations of this invention, the fact that the imaging system is imaging a near-field object, rather than a far-field object, affects the physical location or positioning of the antennas employed for sensing the radiation.

Figure 10:
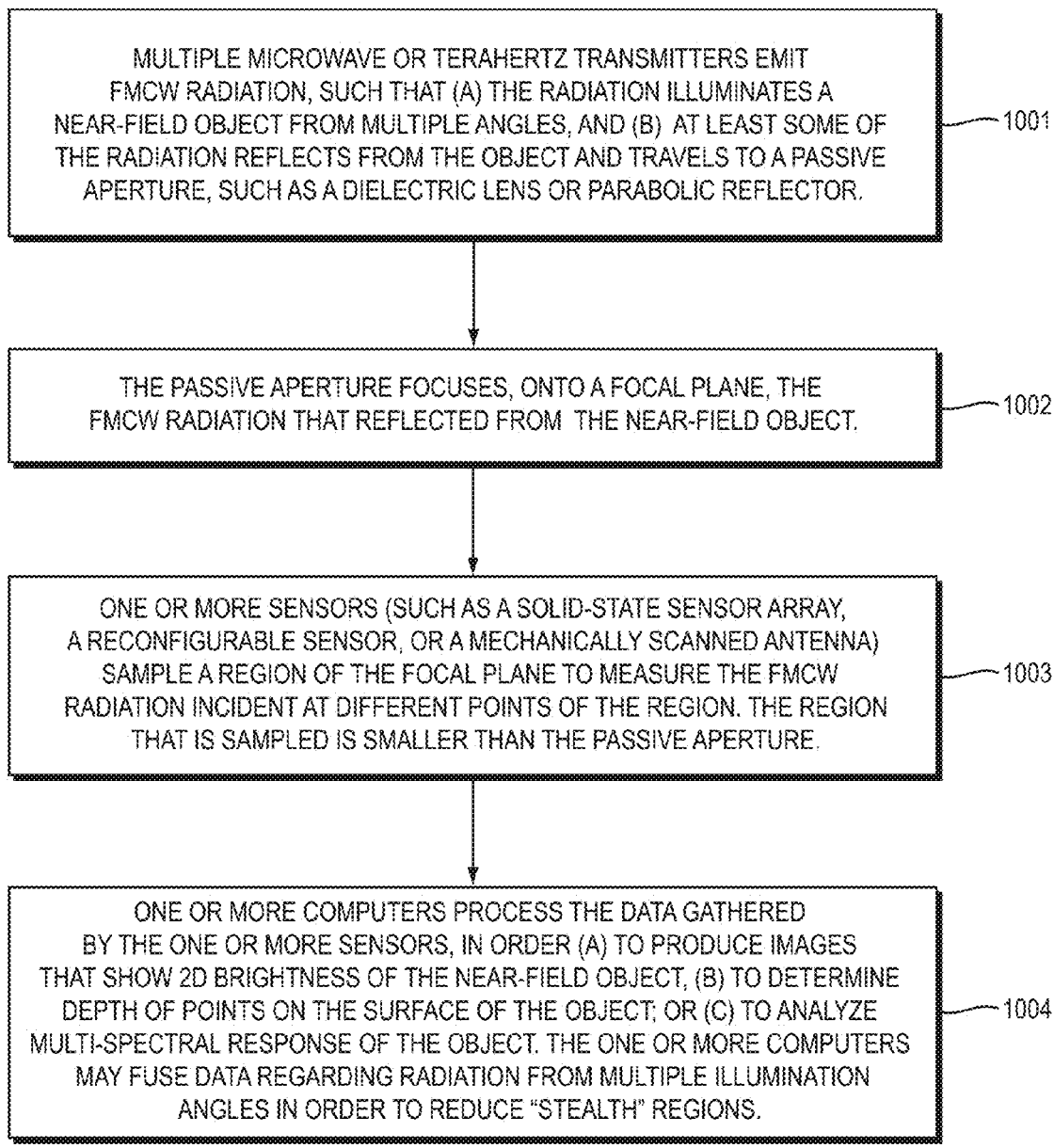
FIG. 10 is a flow chart of an imaging method that involves sampling focused microwave or terahertz radiation.

FIG. 10 is a flow chart of an imaging method that involves sampling focused microwave or terahertz radiation, in an illustrative implementation of this invention. In the example shown in FIG. 10, the method includes the following steps: Multiple transmitters emit FMCW radiation, such that (a) the radiation illuminates a near-field object from multiple angles, and (b) at least some of the radiation reflects from the object and travels to a passive aperture, such as a dielectric lens or parabolic reflector (Step 1001). The passive aperture focuses, onto a focal plane, the FMCW radiation that reflected from the near-field object (Step 1002). One or more sensors (such as a solid-state sensor array, a reconfigurable sensor, or a mechanically scanned antenna) sample a region of the focal plane to measure the FMCW radiation incident at different points of the region. The region that is sampled is smaller than the passive aperture (Step 1003). One or more computers process the data gathered by the one or more sensors, in order (a) to produce images that show 2D brightness of the near-field object, (b) to determine depth of points on the surface of the object; or (c) to analyze multi-spectral response of the object. The one or more computers may fuse data regarding radiation from multiple illumination angles in order to reduce "stealth" regions (Step 1004).

In many implementations of this invention, a passive aperture (e.g., a dielectric lens or a parabolic reflector) focuses the radiation from a near-field object unto a focal plane. However, this invention is not limited to focusing the radiation onto a focal plane. The region onto which the radiation is focused may comprise a curved surface instead.

In many implementations of this invention, one or more dedicated antennas are employed for transmitting the radiation and one or more other dedicated antennas are employed for sensing the radiation that returns from the scene. Alternatively, some or all of the antennas may function as transceivers that, at some times, transmit radiation and at other times detect radiation that returns from the scene.
Software In the Computer Program Listing above, four ASCII text files are listed. The code in these four text files may be saved and run as Matlab® m-files.

The file microwave_camera_read_data.txt comprises software for, among other things, taking raw measurements from the imaging system (from the analog to digital converter) and converting them into a depth cube, with the x axis being left/right, y axis being up/down, and the z axis representing the travel time of the microwave reflections. The file microwave_camera_read_data_cal2.txt comprises software for, among other things, reading sphere calibration data as well as measured data, calibrating the measured data, and plotting it. The file microwave_camera_multispectral_cal4.txt comprises software for, among other things, reading sphere calibration data, measuring data, calibrating in the spectral domain, and plotting it.

The software in the second and third files (microwave_camera_read_data_cal2.txt and microwave_camera_multispectral_cal4.txt) calls on a function mie, which computes (i) the Mie series for a perfect electric conducting sphere, and (ii) the reflectivity of a perfect conducting sphere at a given wavelength. The software compares the ideal Mie values and measured sphere values to calibrate the system. In illustrative implementations of this invention, the software simulates a sphere at various wavelengths over the system's chirp bandwidth, then takes the ratio of the simulated reflectivity to the measured reflectivity and uses that as a calibration to calibrate each range profile acquired by the system.

The file range_boundaries_vectorized.txt comprises a computer program for geometry correction. It takes as input a voxel of uncorrected data from the imaging system, as well as parameters such as transmission location, and outputs the geometry corrected location of this voxel (radius start and end, angle start and end). This geometry correction software is employed to correct the location of each data point captured by the imaging system, for each transmitter and receiver location. Since multiple transmission locations are used, this geometry correction is employed to compare and fuse multiple data-cubes. A raw data-cube is captured with X and Z representing the x and y pixel respectively. The Y axis represents depth. A raw data-cube is a 3D data set. For each voxel, an equivalent geometry-corrected region is found. This region is defined in spherical coordinates in the output.

In the file range_boundaries_vectorized.txt, the outputs of the computer program are as follows: r_low is the lower bound of radius for corrected region (spherical coordinates); r_high is the upper bound of radius for corrected region (spherical coordinates); theta_low is the lower bound of azimuth for corrected region (spherical coordinates); theta_high is the upper bound of azimuth for corrected region (spherical coordinates); phi_low is the lower bound of zenith for corrected region (spherical coordinates); amd phi_high is the upper bound of zenith for corrected region (spherical coordinates)

In the file range_boundaries_vectorized.txt, the inputs of the computer program are as follows: Transmitter is a 3 element vector describing the transmitter location in 3D; Receiver is a 3 element vector describing the receiver location in 3D; focal_plane_distance is the focal plane length of the focusing element; pixel_pitch is the pixel pitch of sampling plane (meters); chirp_bandwidth is the bandwidth of the FMCW chirp; chirp_rate is the slope of the FMCW chirp; fft_length is the length of the digital FFT (1024); sample_rate is the sampling rate of the ADC; v_light is the speed of light (m/s); signal_chain_length is the length of travel between the transmitter, receiver, and internals (excluding wave travel in the scene); num_rows is the number of total pixel rows in original data cube; num_columns is the number of total pixel_columns in the original data cube; pixel_row is a particular pixel row in original data cube; pixel_column is a particular pixel column in original data cube; and frame is a particular depth frame in original data cube.

In some implementations of this invention, a computer performs a program that (i) controls the imaging system to move a scanning antenna to an XY position, and to chirp the data while recording (e.g., at 200KSPS), (ii) converts a real-sampled signal to imaginary using the Hilbert transform, and saves the data into the data cube, and (iii) then moves the scanning antenna to the next XY position. Once it is done running through all XY positions being sampled, this program saves the data cube into a data file (e.g., a .mat file that is easy for Matlab® software to read).

This invention is not limited to the software described in the preceding seven paragraphs. Depending on the particular implementation, the software used in this invention may vary.

Computers

In exemplary implementations of this invention, one or more electronic computers (e.g., servers, network hosts, client computers, integrated circuits, microcontroller, controllers, field-programmable-gate arrays, personal computers, or other onboard or remote computers) are programmed and specially adapted: (1) to control the operation of, or interface with, hardware components of a microwave or terahertz imaging system, including one or more transmitting antennas, one or more receiver antennas, radar controllers, radar front ends, any on-chip radar sensor arrays, any reconfigurable radar sensors, and any actuators for mechanically scanning an antenna in a region onto which radiation is focused; (2) to process data gathered by the one or more receiver antennas to perform depth detection, including to calculate a cross-correlation of a transmitter signal and a received signal; (3) to process data gathered by the one or more receiver antennas to recover, from microwave or terahertz radiation reflected from a near-field object, the 2D brightness, depth, and multi-spectral response of that object, and to determine, from the multi-spectral response, material properties of the object; (4) to perform any other calculation, computation, program, algorithm, or computer function described or implied above; (5) to receive signals indicative of human input; (6) to output signals for controlling transducers for outputting information in human perceivable format; and (7) to process data, to perform computations, to execute any algorithm or software, and to control the read or write of data to and from memory devices (items 1-7 of this sentence referred to herein as the "Computer Tasks"). The one or more computers (e.g. 520, 562, 620, 750) may be in any position or positions within or outside of the imaging system. For example, in some cases (a) at least one computer is housed in or together with other components of the imaging system, and (b) at least one computer is remote from other components of the imaging system. The one or more computers communicate with each other or with other components of the imaging system either: (a) wirelessly, (b) by wired connection, (c) by fiber-optic link, or (d) by a combination of wired, wireless or fiber optic links.

In exemplary implementations, one or more computers are programmed to perform any and all calculations, computations, programs, algorithms, computer functions and computer tasks described or implied above. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium comprises a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, or computer function described or implied above. For example, in some cases, instructions encoded in a tangible, non-transitory, computer-accessible medium comprise instructions for a computer to perform the Computer Tasks.

Network Communication

In illustrative implementations of this invention, a device that includes an electronic component (e.g., devices 102, 103, 104, 514, 516, 518, 520, 521, 522, 523, 524, 525, 550, 562, 620, 710, 720, 750) is configured for wireless or wired communication with other electronic devices in a network.

For example, in some cases, one or more of these devices (e.g., 102, 103, 104, 514, 516, 518, 520, 521, 522, 523, 524, 525, 550, 562, 620, 710, 720, 750) each include a wireless communication module for wireless communication with other electronic devices in a network. Each wireless communication module includes (a) one or more antennas, (b) one or more wireless transceivers, transmitters or receivers, and (c) signal processing circuitry. The wireless communication module receives and transmits data in accordance with one or more wireless standards.

In some cases, one or more of the following hardware components are used for network communication: a computer bus, a computer port, network connection, network interface device, host adapter, wireless module, wireless card, signal processor, modem, router, computer port, cables or wiring.

In some cases, one or more computers (e.g., 520, 562, 620, 750) are programmed for communication over a network. For example, in some cases, one or more computers are programmed for network communication: (a) in accordance with the Internet Protocol Suite, or (b) in accordance with any other industry standard for communication, including any USB standard, ethernet standard (e.g., IEEE 802.3), token ring standard (e.g., IEEE 802.5), wireless standard (including IEEE 802.11 (wi-fi), IEEE 802.15 (bluetooth/zigbee), IEEE 802.16, IEEE 802.20 and including any mobile phone standard, including GSM (global system for mobile communications), UMTS (universal mobile telecommunication system), CDMA (code division multiple access, including IS-95, IS-2000, and WCDMA), or LTS (long term evolution)), or other IEEE communication standard.

Actuators

In illustrative implementations, the imaging system includes actuators. For example, in some cases, one or more actuators translate a scanning antenna to sample different points in a focal plane.

In illustrative implementations, each actuator (including each actuator for actuating any movement) is any kind of actuator, including a linear, rotary, electrical, piezoelectric, electro-active polymer, mechanical or electro-mechanical actuator. In some cases, the actuator includes and is powered by an electrical motor, including any stepper motor or servomotor. In some cases, the actuator includes a gear assembly, drive train, pivot, joint, rod, arm, or other component for transmitting motion. In some cases, one or more sensors are used to detect position, displacement or other data for feedback to one of more of the actuators.

More Definitions

As used herein:

The terms "a" and "an", when modifying a noun, do not imply that only one of the noun exists.

An "antenna" may be of any shape. Non-limiting examples of an "antenna" include (i) a horn antenna or (ii) a rectangular waveguide that does not have a horn attached.

To compute "based on" specified data means to perform a computation that takes the specified data as an input.

Here are some non-limiting examples of a "camera": (a) a digital camera; (b) a digital grayscale camera; (c) a digital color camera; (d) a video camera; (e) a light sensor or image sensor, (f) a set or array of light sensors or image sensors; (g) an imaging system; (h) a light field camera or plenoptic camera; (i) a time-of-flight camera; (j) a depth camera, and (k) an imaging system that includes antennas for imaging in the microwave or terahertz range. A camera includes any computers or circuits that process data captured by the camera.

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. However, a human is not a "computer", as that term is used herein.

"Defined Term" means a term or phrase that is set forth in quotation marks in this Definitions section.

The term "e.g." means for example.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each may be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

"For instance" means for example.

The term "frame" shall be construed broadly. For example, the term "frame" includes measured data about a scene that is captured by an imaging system during a single time period or single exposure, even if (i) the data is not humanly perceptible, (ii) the data has not been computationally processed, and (iii) there is not a one-to-one mapping between the data and the scene being imaged.

In the context of an imaging system: (a) "front" is optically closer to the scene being imaged, and "behind" is optically farther from the scene, during normal operation of the imaging system.

"Herein" means in this document, including text, specification, claims, abstract, and drawings.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

"Intensity" means any measure of or related to intensity, energy or power. For example, the "intensity" of light includes any of the following measures: irradiance, spectral irradiance, radiant energy, radiant flux, spectral power, radiant intensity, spectral intensity, radiance, spectral radiance, radiant exitance, radiant emittance, spectral radiant exitance, spectral radiant emittance, radiosity, radiant exposure or radiant energy density.

"I/O device" means an input/output device. Non-limiting examples of an I/O device include a touch screen, other electronic display screen, keyboard, mouse, microphone, handheld electronic game controller, digital stylus, display screen, speaker, or projector for projecting a visual display.

The "maximum dimension" of an object means the longest Euclidian distance between any two points on the exterior surface of the object.

"Lens" means a single lens, compound lens or system of lens.

As used herein, "microwave frequency band" means the frequency band that is greater than or equal to 300 MHz and less than or equal to 300 GHz.

As used herein, "microwave radiation" means electromagnetic radiation in the microwave frequency band. Thus, as used herein, the term "microwave radiation" includes (a) Ultra High Frequency (UHF) radiation in the 300 MHz to 3 GHz frequency band, (b) Super High Frequency (SHF) radiation in the 3 GHz to 30 GHz frequency band, and (c) Extremely High Frequency (EHF) radiation, which is also known as millimeter wave radiation, in the 30 GHz to 300 GHz frequency band.

As used herein, a "microwave transmitter" means a transmitter that emits microwave radiation. Similarly, a "microwave imaging system" means an imaging system that emits microwave radiation to illuminate a scene and that measures microwave radiation which reflects from the scene.

As used herein, "microwave or terahertz radiation" means electromagnetic radiation in the microwave frequency band or terahertz frequency band. Similarly, a "microwave or terahertz transmitter" means a transmitter that emits microwave or terahertz radiation. Similarly, a "microwave or terahertz imaging system" means an imaging system that emits microwave or terahertz radiation to illuminate a scene and that measures microwave or terahertz radiation which reflects from the scene.

A "near-field object" means, in the context of an imaging system, an object that is at a scene depth relative to the imaging system that is less than $2d^2/\lambda$, where $\lambda$ is wavelength and d is the maximum dimension of the aperture of the imaging system. A "near-field" distance or depth means, in the context of an imaging system, a distance or depth that is less than $2d^2/\lambda$, where $\lambda$ is wavelength and d is the maximum dimension of the aperture of the imaging system.

The term "or" is inclusive, not exclusive. For example, A or B is true if A is true, or B is true, or both A or B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or may be ignored.

"Radiation" means electromagnetic radiation.

As used herein, the term "set" does not include a group with no elements. Mentioning a first set and a second set does not, in and of itself, create any implication regarding whether or not the first and second sets overlap (that is, intersect).

"Some" means one or more.

"Spatial radiation modulator" and "SRM" each mean a device (i) that transmits radiation through the device or reflects radiation from the device, and (ii) that causes a modulation of the intensity, frequency, phase or polarization state of radiation transmitted through or reflected from the device, such that the modulation depends on the spatial position at which the radiation is incident on the device.

As used herein, a "subset" of a set consists of less than all of the elements of the set.

"Substantially" means at least ten percent. For example: (a) 112 is substantially larger than 100; and (b) 108 is not substantially larger than 100.

The term "such as" means for example.

As used herein, "terahertz frequency band" means the frequency band that is greater than 0.3 THz and less than or equal to 390 THz.

As used herein, "terahertz radiation" means electromagnetic radiation in the terahertz frequency band. Similarly, a "terahertz transmitter" means a transmitter that emits terahertz radiation. Similarly, a "terahertz imaging system" means an imaging system that emits terahertz radiation to illuminate a scene and that measures terahertz radiation which reflects from the scene.

To say that a machine-readable medium is "transitory" means that the medium is a transitory signal, such as an electromagnetic wave.

Except to the extent that the context clearly requires otherwise, if steps in a method are described herein, then the method includes variations in which: (1) steps in the method occur in any order or sequence, including any order or sequence different than that described; (2) any step or steps in the method occurs more than once; (3) any two steps may occur the same number of times or a different number of times during the method; (4) any combination of steps in the method is done in parallel or serially; (5) any step in the method is performed iteratively; (6) a given step in the method is applied to the same thing each time that the given step occurs or is applied to different things each time that the given step occurs; or (7) the method includes other steps, in addition to the steps described.

This Definitions section shall, in all cases, control over and override any other definition of the Defined Terms. The Applicant or Applicants are acting as his, her, its or their own lexicographer with respect to the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, the grammatical variations include noun, verb, participle, adjective, and possessive forms, and different declensions, and different tenses.

Variations

This invention may be implemented in many different ways. Here are some non-limiting examples:

In some implementations, this invention is a method comprising: (a) a first set of multiple antennas emitting microwave or terahertz radiation, such that the radiation (i) varies in frequency over time, (ii) illuminates a near-field object, (iii) reflects from the near-field object, and (iv) travels to a reflective or refractive component; (b) the reflective or refractive component focusing, onto a spatial region, the microwave or terahertz radiation that reflected from the near-field object; (c) a second set of one or more antennas taking measurements, in the spatial region, of the microwave or terahertz radiation that reflected from the near-field object and was focused by the reflective or refractive component; and (d) one or more computers calculating, based on the measurements (i) an image of the near-field object, and (ii) depth information regarding the near-field object. In some cases, the reflective or refractive component comprises a parabolic reflector. In some cases, the reflective or refractive component comprises a dielectric lens. In some cases, the focused radiation consists of microwave radiation. In some cases, the focused radiation consists of terahertz radiation. In some cases, the second set of one or more antennas comprises multiple antennas that simultaneously measure the focused radiation. In some cases: (a) the second set of one or more antennas consists of a single antenna; and (b) one or more actuators move the single antenna to measure the focused radiation at different points of the spatial region, each point at a different time. In some cases, the first set of antennas emit the radiation sequentially, one antenna at a time. In some cases, the one or more computers: (a) compute a first set of data cubes, which first set of data cubes comprises a separate data cube for each respective antenna in the first set of antennas, which separate data cube includes data gathered under illumination by the respective antenna; (b) transform the first set of data cubes into a second set of data cubes, such that coordinates of voxels in the second set of data cubes are expressed in a single coordinate system; and (c) compute a combined data cube, by setting intensity for each respective voxel in the combined data cube equal to the maximum intensity for that respective voxel in the second set of data cubes. Each of the cases described above in this paragraph is an example of the method described in the first sentence of this paragraph, and is also an example of an embodiment of this invention that may be combined with other embodiments of this invention.

In some implementations, this invention is an imaging system comprising: (a) a first set of multiple antennas for emitting microwave or terahertz radiation, such that the radiation (i) varies in frequency over time, (ii) illuminates a near-field object, and (iii) reflects from the near-field object; (b) a reflective or refractive component for focusing, onto a spatial region, the microwave or terahertz radiation that reflected from the near-field object; (c) a second set of one or more antennas for taking measurements, in the spatial region, of the microwave or terahertz radiation that reflected from the near-field object and was focused by the reflective or refractive component; and (d) one or more computers that are programmed to calculate, based on the measurements (i) an image of the near-field object, and (ii) depth information regarding the near-field object. In some cases, the reflective or refractive component comprises a parabolic reflector. In some cases, the reflective or refractive component comprises a dielectric lens. In some cases, the one or more computers are programmed to cause the first set of antennas to emit the microwave or terahertz radiation as a frequency-modulated continuous-wave signal. In some cases, the imaging system further comprises a programmable mask that is positioned behind the reflective or refractive component and in front of the second set of one or more antennas. In some cases, the second set of one or more antennas comprise multiple antennas that simultaneously measure the focused radiation. In some cases: (a) the second set of one or more antennas consists of a single antenna; and (b) the imaging system further comprises one or more actuators for moving the single antenna to measure the focused radiation at different points of the spatial region, each point at a different time. In some cases, the one or more computers are programmed: (a) to control the first set of antennas, such that the first set of antennas emit the microwave or terahertz radiation sequentially, one antenna at a time; (b) to compute a first set of data cubes, which first set of data cubes comprises a separate data cube for each respective antenna in the first set of antennas, which separate data cube includes data gathered under illumination by the respective antenna; (c) to transform the first set of data cubes into a second set of data cubes, such that coordinates of voxels in the second set of data cubes are expressed in a single coordinate system; and (d) to compute a combined data cube, by setting intensity for each respective voxel in the combined data cube equal to the maximum intensity for that respective voxel in the second set of data cubes. Each of the cases described above in this paragraph is an example of the imaging system described in the first sentence of this paragraph, and is also an example of an embodiment of this invention that may be combined with other embodiments of this invention.

In some implementations, this invention is an imaging system comprising: (a) a first set of multiple antennas for emitting microwave or terahertz radiation, such that the radiation (i) illuminates a near-field object, and (ii) reflects from the near-field object; (b) a reflective or refractive component for focusing, onto a spatial region, the microwave or terahertz radiation that reflected from the near-field object; (c) a second set of one or more antennas for taking measurements, in the spatial region, of the microwave or terahertz radiation that reflected from the near-field object; and (d) one or more computers that are programmed to calculate, based on the measurements (i) an image of the near-field object, and (ii) depth information regarding the near-field object. In some cases, the reflective or refractive component comprises a dielectric lens. In some cases, the reflective or refractive component comprises a parabolic reflector. Each of the cases described above in this paragraph is an example of the imaging system described in the first sentence of this paragraph, and is also an example of an embodiment of this invention that may be combined with other embodiments of this invention.

The above description (including without limitation any attached drawings and figures) describes illustrative implementations of the invention. However, the invention may be implemented in other ways. The methods and apparatus which are described above are merely illustrative applications of the principles of the invention. Other arrangements, methods, modifications, and substitutions by one of ordinary skill in the art are therefore also within the scope of the present invention. Numerous modifications may be made by those skilled in the art without departing from the scope of the invention. Also, this invention includes without limitation each combination and permutation of one or more of the abovementioned implementations, embodiments and features.

What is claimed is:

1. A method comprising:
   (a) a first set of multiple antennas emitting microwave or terahertz radiation, in such a way that the radiation
      (i) varies in frequency over time,
      (ii) illuminates a near-field object,
      (iii) reflects from the near-field object, and
      (iv) travels to a reflective or refractive component;
   (b) the reflective or refractive component focusing, onto a spatial region, the microwave or terahertz radiation that reflected from the near-field object;
   (c) a second set of one or more antennas taking measurements, in the spatial region, of the microwave or terahertz radiation that reflected from the near-field object and was focused by the reflective or refractive component; and
   (d) one or more computers calculating, based on the measurements
      (i) an image of the near-field object, and
      (ii) depth information regarding the near-field object
   wherein
   (i) the second set of one or more antennas consists of a single antenna, and
   (ii) the method further comprises one or more actuators moving the single antenna to measure the focused radiation at different points of the spatial region, each point at a different time.

2. A method comprising:
   (a) a first set of multiple antennas emitting microwave or terahertz radiation, in such a way that the radiation
      (i) varies in frequency over time,
      (ii) illuminates a near-field object,
      (iii) reflects from the near-field object, and
      (iv) travels to a reflective or refractive component;
   (b) the reflective or refractive component focusing, onto a spatial region, the microwave or terahertz radiation that reflected from the near-field object;
   (c) a second set of one or more antennas taking measurements, in the spatial region, of the microwave or terahertz radiation that reflected from the near-field object and was focused by the reflective or refractive component; and
   (d) one or more computers calculating, based on the measurements
      (i) an image of the near-field object, and
      (ii) depth information regarding the near-field object
   wherein
   (i) the first set of antennas emit the radiation sequentially, one antenna at a time, and
   (ii) the one or more computers
      (A) compute a first set of data cubes, which first set of data cubes comprises a separate data cube for each respective antenna in the first set of antennas, which separate data cube includes data gathered under illumination by the respective antenna,
      (B) transform the first set of data cubes into a second set of data cubes, in such a way that coordinates of voxels in the second set of data cubes are expressed in a single coordinate system, and
      (C) compute a combined data cube, by setting intensity for each respective voxel in the combined data cube equal to the maximum intensity for that respective voxel in the second set of data cubes.

3. An imaging system comprising:
   (a) a first set of multiple antennas for emitting microwave or terahertz radiation, in such a way that the radiation
      (i) varies in frequency over time,
      (ii) illuminates a near-field object, and
      (iii) reflects from the near-field object;
   (b) a reflective or refractive component for focusing, onto a spatial region, the microwave or terahertz radiation that reflected from the near-field object;
   (c) a second set of one or more antennas for taking measurements, in the spatial region, of the microwave or terahertz radiation that reflected from the near-field object and was focused by the reflective or refractive component; and
   (d) one or more computers that are programmed to calculate, based on the measurements
      (i) an image of the near-field object, and
      (ii) depth information regarding the near-field object;
   wherein
   (i) the second set of one or more antennas consists of a single antenna, and
   (ii) the imaging system further comprises one or more actuators for moving the single antenna to measure the focused radiation at different points of the spatial region, each point at a different time.

4. An imaging system comprising:
   (a) a first set of multiple antennas for emitting microwave or terahertz radiation, in such a way that the radiation
      (i) varies in frequency over time,
      (ii) illuminates a near-field object, and
      (iii) reflects from the near-field object;
   (b) a reflective or refractive component for focusing, onto a spatial region, the microwave or terahertz radiation that reflected from the near-field object;
   (c) a second set of one or more antennas for taking measurements, in the spatial region, of the microwave or terahertz radiation that reflected from the near-field object and was focused by the reflective or refractive component; and
   (d) one or more computers that are programmed to calculate, based on the measurements
      (i) an image of the near-field object, and
      (ii) depth information regarding the near-field object;
   wherein the one or more computers are programmed
      (i) to control the first set of antennas, in such a way that the first set of antennas emit the microwave or terahertz radiation sequentially, one antenna at a time,
      (ii) to compute a first set of data cubes, which first set of data cubes comprises a separate data cube for each respective antenna in the first set of antennas, which separate data cube includes data gathered under illumination by the respective antenna,
      (iii) to transform the first set of data cubes into a second set of data cubes, in such a way that coordinates of voxels in the second set of data cubes are expressed in a single coordinate system, and
      (iv) to compute a combined data cube, by setting intensity for each respective voxel in the combined data cube equal to the maximum intensity for that respective voxel in the second set of data cubes.

* * * * *